US010815257B2

United States Patent
Dini et al.

(12)

(10) Patent No.: US 10,815,257 B2
(45) Date of Patent: Oct. 27, 2020

(54) POLYMORPH OF SODIUM NERIDRONATE AND PREPARATION PROCESS THEREOF

(71) Applicant: ABIOGEN PHARMA S.P.A., Pisa (IT)

(72) Inventors: Laura Dini, Pisa (IT); Fabio Neggiani, Pisa (IT); Barbara Politi, Leghorn (IT); Stefano Luca Giaffreda, Bologna (IT); Alex Petrolati, Senigallia (IT); Michel Chiarucci, Castenaso (IT); Serena Fabbroni, Medicina (IT); Kesheng Zhang, Lenzburg (CH); Michael Roeder, Gomaringen (DE)

(73) Assignee: ABIOGEN PHARMA S.P.A., Pisa (IT)

( * ) Notice: Subject to any disclaimer, the term of this patent is extended or adjusted under 35 U.S.C. 154(b) by 0 days.

(21) Appl. No.: 16/379,873

(22) Filed: Apr. 10, 2019

(65) Prior Publication Data

US 2019/0308999 A1    Oct. 10, 2019

(30) Foreign Application Priority Data

Apr. 10, 2018  (EP) .................................... 18166508

(51) Int. Cl.
| | |
|---|---|
| *C07F 9/38* | (2006.01) |
| *A61P 5/20* | (2006.01) |
| *A61P 19/02* | (2006.01) |
| *A61P 3/14* | (2006.01) |
| *A61P 35/04* | (2006.01) |
| *A61P 19/10* | (2006.01) |
| *C07F 9/02* | (2006.01) |
| *A61K 31/663* | (2006.01) |

(52) U.S. Cl.
CPC .......... *C07F 9/3873* (2013.01); *A61K 31/663* (2013.01); *A61P 3/14* (2018.01); *A61P 5/20* (2018.01); *A61P 19/02* (2018.01); *A61P 19/10* (2018.01); *A61P 35/04* (2018.01); *C07F 9/025* (2013.01); *C07B 2200/13* (2013.01)

(58) Field of Classification Search
CPC .................................................... C07F 9/3873
See application file for complete search history.

(56) References Cited

U.S. PATENT DOCUMENTS 4,304,734 A    12/1981 Jary et al.

FOREIGN PATENT DOCUMENTS

WO    2008004000 A1    1/2008

OTHER PUBLICATIONS

Extended European Search Report and of priority application No. 18166508A dated Sep. 25, 2018.
Kieczykowski G.R., "Preparation of (4-amino-1-hydroxybutylidene)bisphosphonic acid sodium salt, MK217 (alendronate sodium). An improved procedure for the preparation of 1-hydroxy-1,1-bisphosphonic acids", Journal of Organic Chemistry, vol. 60, No. 25, 1995, pp. 8310-8312.
Lenin R., et al., "Microwave-assisted efficient synthesis of bisphosphonate libraries: a useful procedure for the preparation of bisphosphonates containing nitrogen and sulfur", Medicinal Chemistry Research, vol. 22, 2013, pp. 1624-1629.
Response to the European Extended Search Report and European Search Opinion dated Apr. 10, 2019.

*Primary Examiner* — Joseph R Kosack
(74) *Attorney, Agent, or Firm* — Silvia Salvadori, P.C.; Silvia Salvadori

(57) ABSTRACT

The present invention relates to a novel crystalline hemihydrate polymorph of neridronic acid sodium salt, and a novel process for the preparation thereof comprising the steps of: 1) dissolving solid sodium neridronate in any crystalline form in water, at a temperature in the range from 70 to 90° C., to obtain an aqueous solution of sodium neridronate; 2) adding a solvent selected from the group consisting in ethanol, 1-propanol, and 2-propanol to the aqueous solution obtained from step (1), so that the final water:solvent volume ratio is in the range from 1:0.5 to 1:1, thus obtaining a suspension; 3) placing the suspension obtained from step (2) under mechanical stirring, at a temperature in the range from 60 to 95° C.; 4) recovering the crystalline hemihydrate form F of sodium neridronate formed in the previous step (3). The crystalline hemihydrate form F of sodium neridronate, particularly stable, may be employed in the preparation of solid oral pharmaceutical forms for use in the treatment of musculoskeletal and calcium metabolism disorders.

20 Claims, 13 Drawing Sheets

POLYMORPH OF SODIUM NERIDRONATE AND PREPARATION PROCESS THEREOF

This Non-Provisional application claims priority to and the benefit of European Application No. 18166508.4 filed on Apr. 10, 2018, the content of which is incorporated herein by reference in its entirety.

FIELD OF THE INVENTION

The present invention relates to a crystalline hemihydrate polymorph of sodium neridronate, a process for the preparation thereof, and pharmaceutical forms comprising it.

STATE OF THE ART

Sodium Neridronate is the sodium salt of Neridronic Acid, whose IUPAC name is 6-amino-1-hydroxy-1,1-hexane-diphosphonic acid.

Sodium neridronate is represented by the following structural formula:

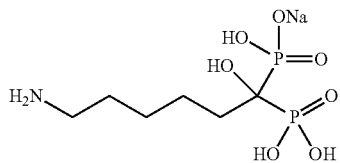

Neridronic acid belongs to the group of bisphosphonates, in particular of aminobisphosphonates.

Bisphosphonic acids, in particular aminobisphosphonic acids, and pharmaceutically acceptable salts thereof, are an important class of drugs useful for the treatment of various musculoskeletal and calcium metabolism disorders.

In particular, therapeutic properties of bisphosphonates depend on their high affinity for hydroxyapatite crystals, main constituents of bones, to which these molecules bind preventing their reabsorption.

Bisphosphonates are therefore widely used in clinical practice to treat diseases such as osteoporosis, hyperparathyroidism, hypercalcemia of malignancy, osteolytic bone metastases, myositis ossificans progressiva, universal calcinosis, arthritis, neuritis, bursitis, tendinitis, Paget's disease, osteogenesis imperfecta, Complex Regional Pain Syndrome (CRPS) or algodystrophy, and other inflammatory diseases.

Sodium neridronate, specifically in injectable form for intramuscular or intravenous administration, has been used successfully for several years in the treatment of osteogenesis imperfecta, Paget's bone disease, and algodystrophy.

In order to improve the compliance of these drugs, and therefore facilitate their intake by patients, it would be desirable to have solid forms to be administered orally.

The possibility to make solid pharmaceutical forms for oral administration is in general terms linked to the availability of active pharmaceutical ingredients with suitable stability characteristics in the solid state.

For this reason, the possibility to make pharmaceutical preparations based on sodium neridronate, in solid form, to be administered orally is tightly correlated with the availability of the active ingredient sodium neridronate in a solid form stable over time.

Sodium neridronate, according to prior art, may be prepared as described in WO2008/004000, in particular in Example 4, where the preparation of the sodium salt of neridronic acid is carried out starting from a mixture of 6-aminohexanoic acid and phosphorous acid in acetonitrile. In particular, the salt would be obtained from the reaction mixture by cooling it at 55-65° C., and adding sodium hydroxide up to pH 4.4-4.8, followed by cooling it to 25-35° C., separating the aqueous phase containing sodium neridronate from the phase containing acetonitrile, adding acetone to said aqueous phase, and further cooling said phase to 0-5° C. for 3 hours; the precipitated sodium neridronate is filtered off, washed, first with water and then with methanol, until a wet sodium neridronate solid is obtained, to be dried. According to the invention, at the end of the drying process, a white powder is obtained with melting temperature (with decomposition) comprised between 232 and 239° C.

The inventors of the present invention, while reproducing the synthesis described in WO2008/004000, discovered that it leads to the obtainment of a particular polymorphic form, not described in the prior art, and in particular not even in WO2008/004000, which was by them conventionally designated "Form E", wherein the salt is in a tetrahydrate form, and during the stability studies carried out by the present inventors it didn't provide the adequate performance required for its use in the preparation of solid oral forms, as highlighted in the experimental examples below.

Another disclosure present in the prior art, which does not report, however, any synthetic detail in relation to the specific preparation of sodium neridronate, is EP0494844 owned by Istituto Gentili Spa, which describes a novel synthesis of aminobiphosphonic acids, feasible at an industrial level, wherein the possibility of preparing the corresponding lithium, sodium or potassium salts, starting from diluted solutions of bisphosphonic acid by means of a neutralization reaction, carried out at 80° C., in the presence of a diluted solution of the corresponding alkali hydroxides is mentioned. While reproducing the synthesis described in this patent, starting from neridronic acid synthesized according to the Examples 1 and 2 of the patent, reporting the use of different molar ratios between phosphorous acid and phosphorus trichloride reagents, the inventors of the present invention obtained two different solid forms of sodium neridronate, the same "Form E" already obtained under the synthesis conditions of the previous patent WO2008/004000 adopting the conditions of Example 1, and a novel solid form, conventionally designated as "Form B", wherein the salt was in a monohydrate form, when they adopted the conditions described in Example 2, respectively. This second polymorphic form B, during the stability studies performed by the present inventors, also did not provide the appropriate performance required for its use in the preparation of solid oral forms.

Likewise, many other patent documents describe the optimization of preparative syntheses, also at an industrial level, of bisphosphonic acids, including in particular also 6-amino bisphosphonic acid (neridronic acid), but none of them details the synthesis of the specific sodium salt of neridronic acid.

Some specific industrial synthesis methods of neridronic acid sodium salt, currently secret, have been developed over time by the owner of the present invention, Abiogen Pharma SpA, which is today the only company worldwide producing and selling drugs based on sodium neridronate, in injectable form.

As will be better described hereinafter, the synthetic processes used up to now by the owner of the present patent application lead, likewise the processes described so far in the prior art, to the same crystalline polymorphic forms of sodium neridronate "Form B" and "Form E", never described so far in the literature, and which do not however show adequate stability performance to be used in the preparation of solid oral forms.

The problem of identifying a sufficiently stable solid form of sodium neridronate to be used in the preparation of solid oral pharmaceutical forms remains, therefore, unsolved.

One of the objects of the present invention is, therefore, to provide a novel solid form of sodium neridronate characterized by a greater stability than that of the forms resulting from the syntheses of the prior art.

Accordingly, a further object of the present invention is to provide a reproducible industrial process for the preparation of said stable solid form of sodium neridronate.

Finally, still a further object of the present invention is to provide pharmaceutical compositions comprising it.

SUMMARY OF THE INVENTION

The inventors of the present patent application have identified said novel stable solid form of sodium neridronate in a novel crystalline hemihydrate form of sodium neridronate, conventionally designated by the inventors "Form F".

The present invention therefore relates to a novel crystalline hemihydrate polymorph of sodium neridronate, said "Form F" of sodium neridronate, showing an X-ray powder diffraction spectrum (XRPD) with characteristic peaks at 2θ angle values of 6.51°, 12.02°, 16.51°, 16.66°, 20.80°, 22.21°, 25.30°, 27.65°, 30.05°, 31.87°.

Said crystalline hemihydrate form F of sodium neridronate crystallizes in a monoclinic system with the following cell parameters: a=14.3749 (3) Å, b=8.76600 (10) Å, c=21.2927 (4) Å, α=90°, β=109.339 (2)°, γ=90°, V=2531.71 (8) Å$^3$, with P21/c space group.

In a second aspect thereof, the invention provides a process for the preparation of the novel crystalline polymorphic hemihydrate form F of sodium neridronate, characterized by comprising the following steps:

1) dissolving solid sodium neridronate in any crystalline form in water, at a temperature in the range from 70 to 90° C., to obtain an aqueous solution of sodium neridronate;

2) adding a solvent selected from the group consisting in ethanol, 1-propanol, and 2-propanol to the aqueous solution obtained from step (1), so that the final water:solvent volume ratio is in the range from 1:0.5 to 1:1, thus obtaining a suspension;

3) placing the suspension obtained from step (2) under mechanical stirring, at a temperature in the range from 60 to 95° C.;

4) recovering the crystalline hemihydrate Form F of sodium neridronate formed in the previous step (3).

Preferably, in step (2) of the process of the invention ethanol is used as solvent.

Advantageously, said preparation process of crystalline hemihydrate form F of sodium neridronate may be applied downstream of any sodium neridronate synthesis process described in the prior art, being able to carry out the conversion of any solid form deriving from said synthetic processes of the prior art into the crystalline hemihydrate form F of sodium neridronate.

In a third aspect thereof, the preparation process of the novel crystalline hemihydrate Form F of sodium neridronate may be applied downstream of a novel synthetic process for obtaining sodium neridronate comprising the following steps:

a) reacting 6-aminohexanoic acid with a mixture of phosphorous acid and methanesulfonic acid, and obtain a mixture;

b) adding phosphorus trichloride to said mixture in step (a) under stirring and at a temperature in the range from 60 to 80° C., keeping the mixture obtained under stirring at a temperature in the range from 60 to 70° C. for at least 15 hours;

c) diluting the mixture obtained in the previous step (b) with water, and heating said mixture diluted with water to a temperature in the range from 90 to 120° C. for at least 13 hours, obtaining a heated mixture;

d) cooling the heated mixture obtained from step (c) to a temperature below 75° C., and slowly adding sodium hydroxide to a pH in the range from 3 to 5, obtaining a suspension;

e) cooling the suspension obtained in step (d) to a temperature in the range from 10 to 30° C., then slowly adding ethanol to obtain the precipitation of the sodium salt of sodium neridronate in any crystalline form;

f) recovering the sodium neridronate in any crystalline form formed in the previous step (e).

In one advantageous aspect, therefore, the preparation process of the novel crystalline polymorph hemihydrate Form F of sodium neridronate may be applied downstream of the novel synthetic process for obtaining sodium neridronate starting from sodium neridronate in any crystalline form.

In a fourth aspect thereof, the present invention provides pharmaceutical compositions comprising the crystalline polymorph hemihydrate Form F of sodium neridronate, and pharmaceutically acceptable vehicles.

Finally, in a fifth aspect thereof, the present invention provides therapeutic uses and therapeutic treatment methods employing the pharmaceutical compositions comprising the crystalline polymorph hemihydrate form F of sodium neridronate.

DETAILED DESCRIPTION OF THE INVENTION

The inventors of the present patent application have identified a novel stable solid form of sodium neridronate in a novel crystalline hemihydrate form of sodium neridronate, conventionally designated "form F" by the inventors, with which it is possible to solve the technical problem related to the preparation of pharmaceutical compositions in solid oral dosage form.

Figure 3:
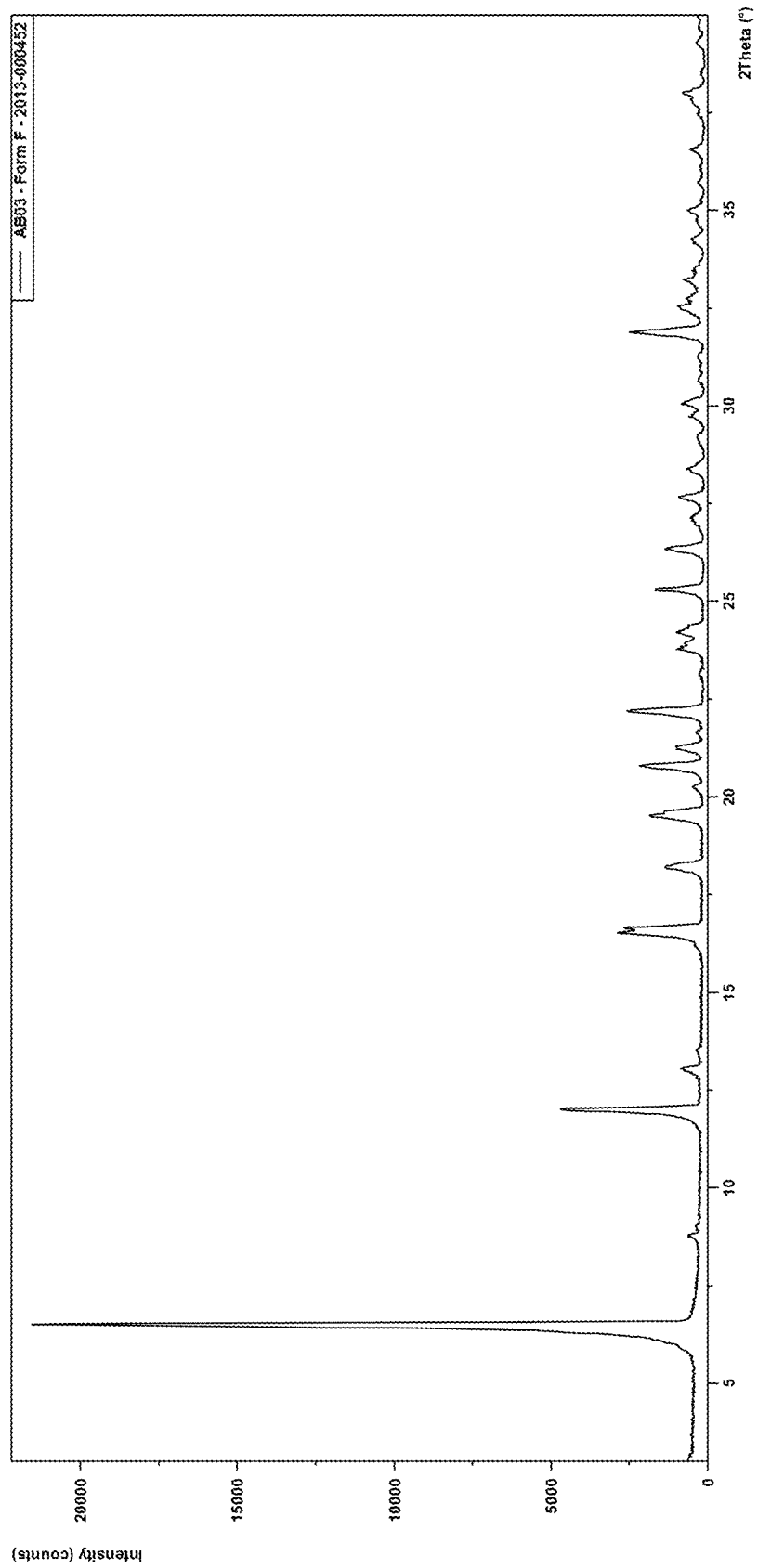
FIG. 3: XRPD of the crystalline polymorphic form F of sodium neridronate.

In a first aspect thereof, the present invention therefore relates to a novel crystalline hemihydrate polymorph of sodium neridronate, named "form F" of sodium neridronate, which has an X-ray powder diffraction spectrum (XRPD) with peaks at characteristic 2θ angle values of 6.51°, 12.02°, 16.51°, 16.66°, 20.80°, 22.21°, 25.30°, 27.65°, 30.05°, 31.87°, as apparent in FIG. 3.

These peaks do not correspond to any characteristic group of peaks of various polymorphs obtainable by the known synthesis processes, which give rise to polymorphic crystalline forms conventionally designated by the inventors with form E and form B wording (FIG. 1 and FIG. 2), moreover never described in the prior art and first detected and characterized by the inventors.

In particular, in FIG. 3 diffractogram of the crystalline polymorphic hemihydrate form F, characteristic peaks of the crystalline polymorphic hemihydrate form F of sodium neridronate can be highlighted, which are completely absent in the spectra of the other crystalline polymorphs of sodium neridronate, form E and B cited; this evidence is important because it allows us to state that the crystalline hemihydrate form F of interest can never be obtained, even in a mixture, from the synthetic processes described in the prior art.

Accordingly, FIG. 3 diffractogram cannot be associated with any of the polymorphic forms obtainable from the previously described syntheses.

Figure 5:
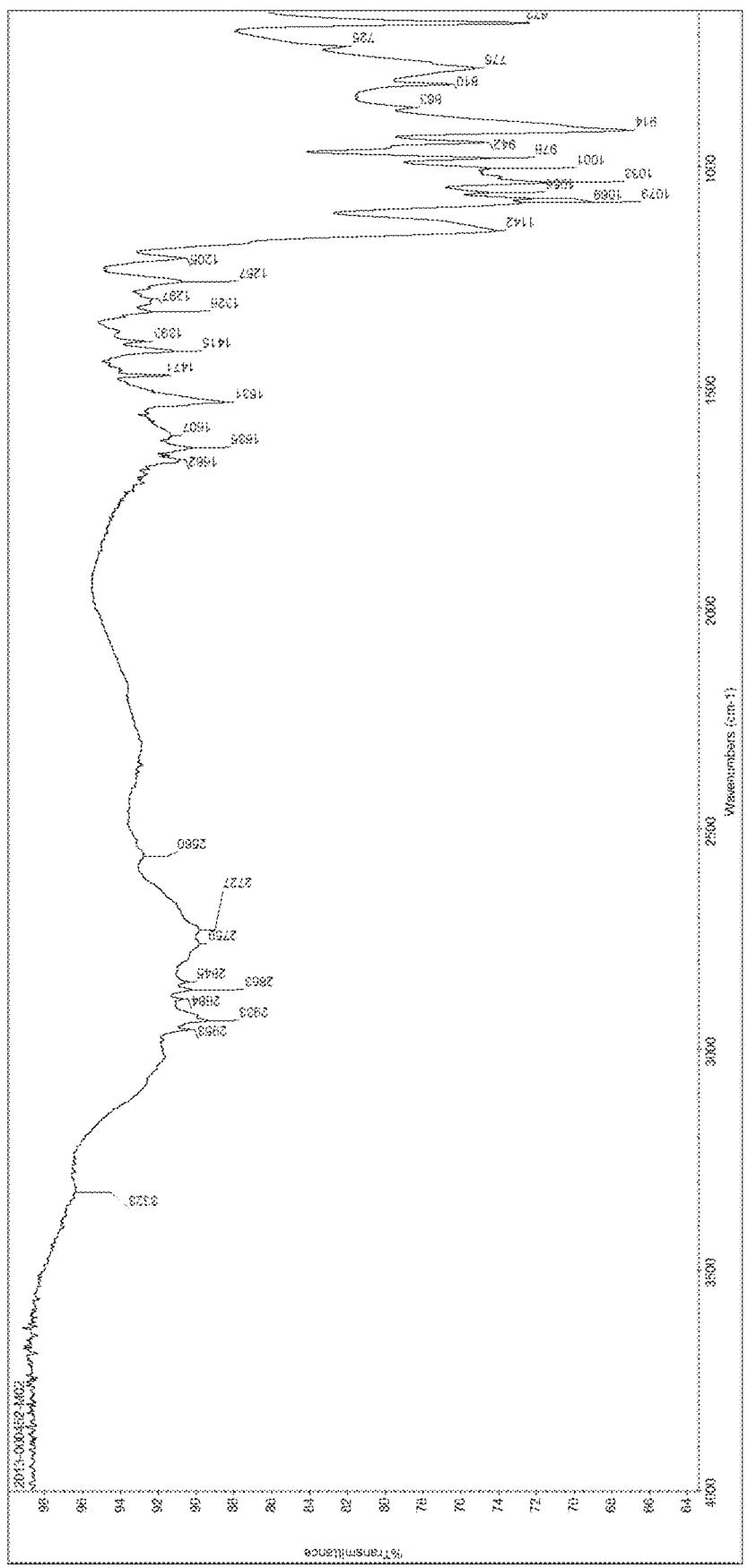
FIG. 5: FT-IR of the crystalline polymorphic hemihydrate form F of sodium neridronate.

The crystal of the crystalline polymorphic hemihydrate form F of sodium neridronate crystallizes in a monoclinic system with the following cell parameters: a=14.3749 (3) Å, b=8.76600 (10) Å, c=21.2927 (4) Å, α=90°, β=109.339 (2)°, γ=90°, V=2531.71 (8) Å3, with P21/c space group. The crystalline polymorphic hemihydrate form F of sodium neridronate is also characterized by a typical infrared spectrum, acquired using an infrared spectrometer based on the Fourier transform (FT-IR), as shown in FIG. 5.

Figure 6:
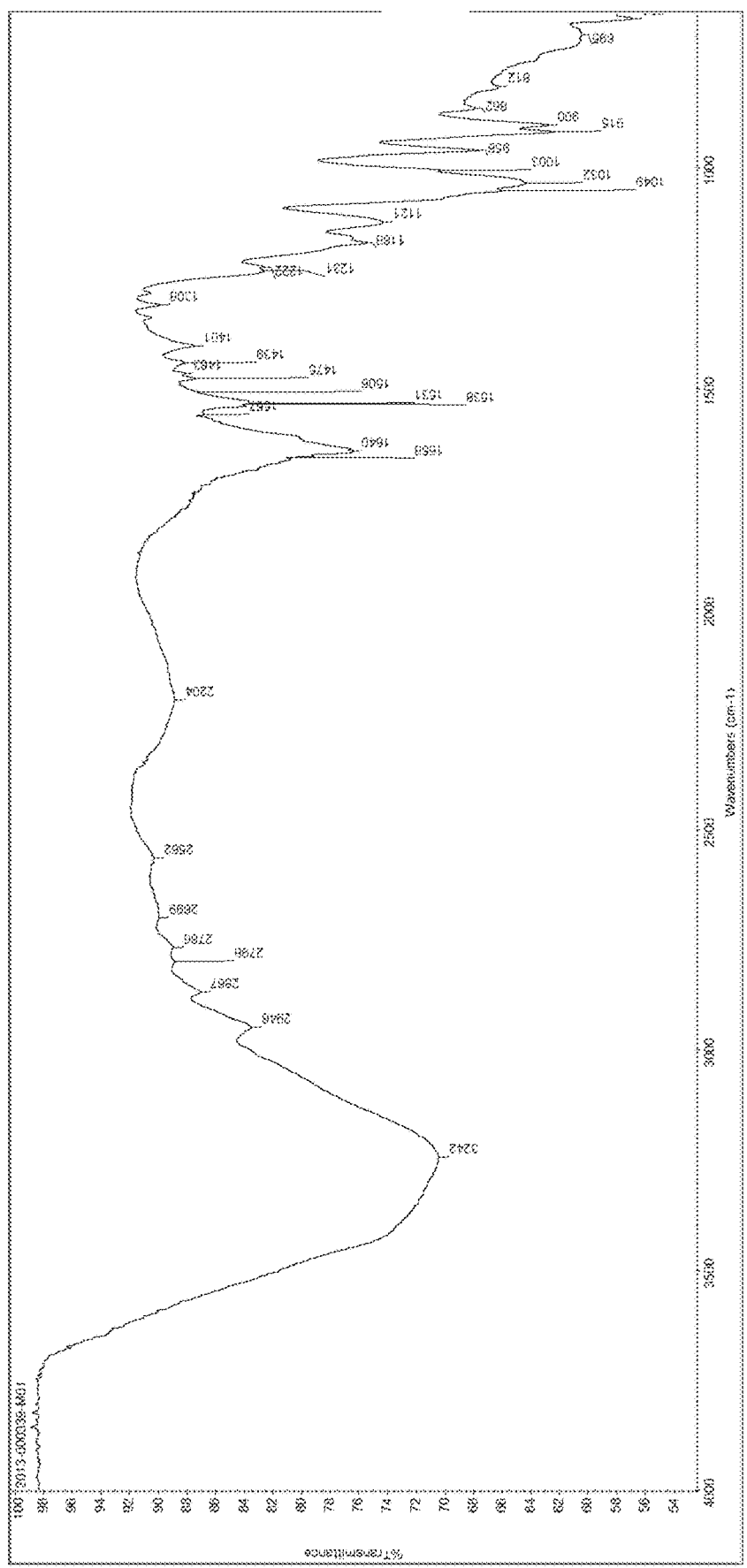
FIG. 6: FT-IR of the crystalline polymorphic form E of sodium neridronate.
Figure 7:
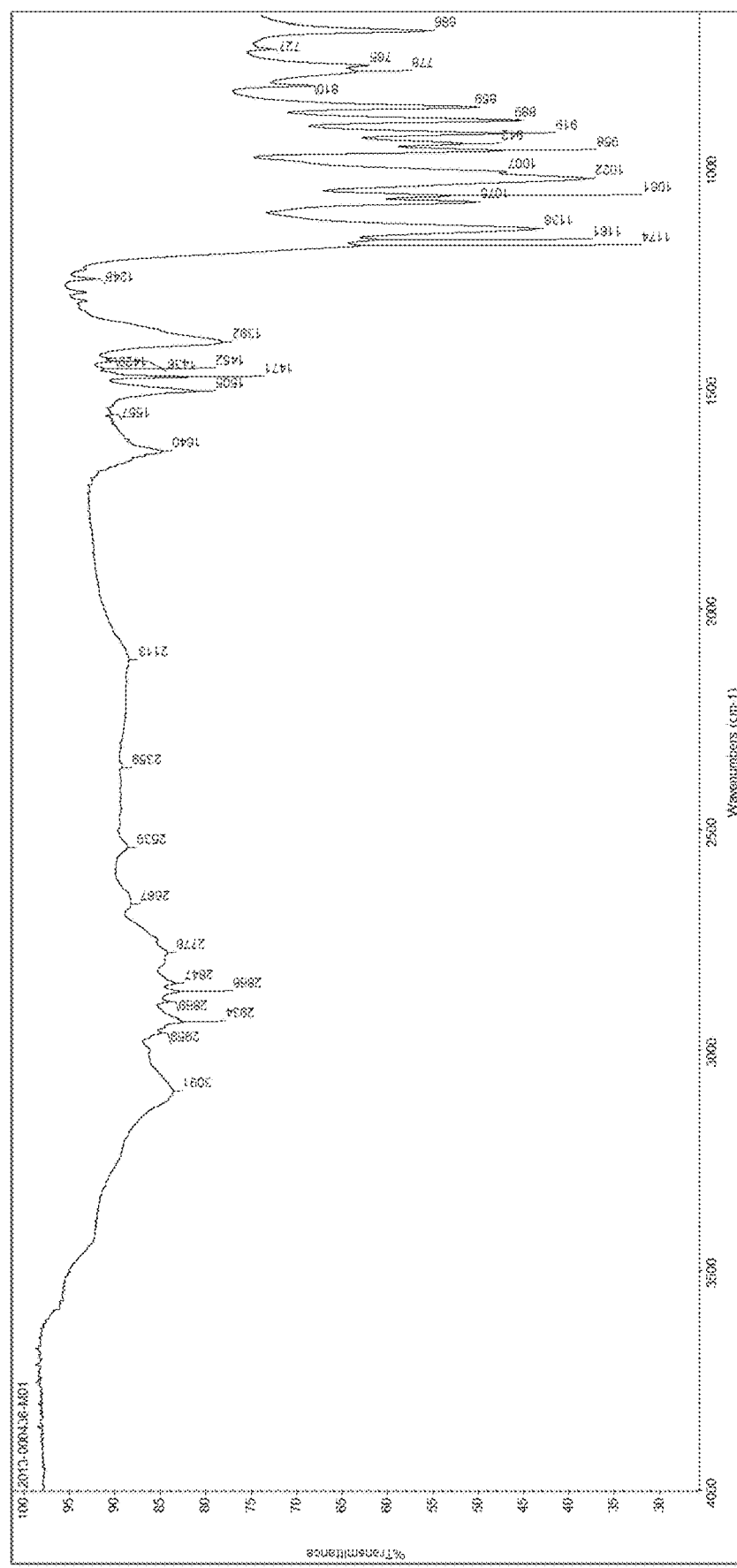
FIG. 7: FT-IR of the crystalline polymorphic form B of sodium neridronate.

In this spectrum, characteristic peaks of the crystalline polymorph hemihydrate form F of sodium neridronate can also be highlighted, which are completely absent in the spectra of the crystalline polymorphs, form E and form B, of sodium neridronate obtainable by the prior art synthesis procedures (in FIG. 6 and FIG. 7, respectively). FT-IR spectroscopy also confirms, therefore, the absolute novelty of the crystalline hemihydrate form F of sodium neridronate, and the fact that it had never been obtained before, not even in trace or mixture together with the products of the prior art syntheses.

The novel crystalline polymorphic hemihydrate form F of sodium neridronate, as indicated in the preamble and as will be clear from the following examples, has therefore proved to be particularly stable and thus suitable for the purposes of the present invention.

The preparation of oral solid pharmaceutical forms of sodium neridronate cannot, in fact, prescind from the use of a form of the active ingredient sodium neridronate exhibiting adequate stability characteristics in crystalline form, to be able to be handled and stored over time without leading to hygroscopicity and instability phenomena.

As will be clear from the following examples, wherein the chemical-physical behaviors of the crystalline forms E and B, obtainable from the prior art syntheses, were compared with the crystalline hemihydrate form F obtained from the synthesis which will be described below, said crystalline forms E and B, due to apparent instability and hygroscopicity, could not have been used as raw materials for the preparation of solid oral forms of sodium neridronate.

Otherwise, the crystalline hemihydrate form F, unexpectedly and surprisingly exhibited an original chemical-physical behavior, said crystalline form being successful in permanently preserving its structure even in extremely critical experimental conditions such as, for example, in the presence of relative humidity values (RH) of 90% at a temperature of 25° C., or relative humidity values (RH) of 75% at a temperature of 40° C.

In the various experimental conditions tested, the crystalline hemihydrate form F has always proved to be perfectly stable, and therefore usable as a solid form for the preparation of solid oral pharmaceutical forms based on sodium neridronate.

In order to prepare said stable crystalline hemihydrate form F of sodium neridronate, the inventors of the present invention developed a surprisingly simple, effective, and reproducible process, that allows to obtain said crystalline hemihydrate form F starting from any available solid form of sodium neridronate, and therefore, for example, starting from form E or form B of sodium neridronate as obtainable from prior art syntheses, said process being characterized by comprising the following steps:

1) dissolving solid sodium neridronate in any crystalline form in water, at a temperature in the range from 70 to 90° C., to obtain an aqueous solution of sodium neridronate;

2) adding a solvent selected from the group consisting in ethanol, 1-propanol, and 2-propanol to the aqueous solution obtained from step (1), so that the final water:solvent volume ratio is in the range from 1:0.5 to 1:1, thus obtaining a suspension;

3) placing the suspension obtained from step (2) under mechanical stirring, at a temperature in the range from 60 to 95° C.;

4) recovering the crystalline hemihydrate form F of sodium neridronate formed in the previous step (3).

For the purposes of the present invention, step (3), wherein the suspension consisting of sodium neridronate dispersed in the mixture of water and solvent is kept under stirring for a given time and at a given temperature, is also referred to as the slurry step.

Preferably the dissolution step (1) is carried out at a temperature in the range from 75 to 85° C.

Typically, the dissolution step (1) of sodium neridronate in water is carried out under stirring and has a duration in the range from 15 to 180 minutes.

Advantageously, after step (1) and before step (2), the solution of step (1) is subjected to filtration, typically with preheated activated carbon filters, preferably at a temperature from 75 to 85° C., in order to remove any sodium neridronate crystals remained undissolved. When said filtration is performed, the reactor is washed with water to optimize the dissolution and therefore the recovery of all the sodium neridronate crystals, said washing water is passed through the same filters, and the filtered washing water combined with the solution of step (1).

Preferably, ethanol is used as a solvent in step (2) of the process of the invention. Moreover, advantageously, a reduced solvent content is used, in view of a reduction of both managing costs and environmental impact, whereby the final water:solvent volume ratio in step (2) is preferably comprised in the range from 1:0.5 to 1:0.8. Preferably, the slurry step (3) is carried out at a temperature in the range from 70 to 90° C., more preferably from 75 to 85° C.

Typically, the slurry step (3) has a duration of from 2 to 80 hours, preferably from 10 to 20 hours, and the higher the conduction temperature the faster the slurry step (3) is.

The process of the invention also proceeds with excellent yields at any temperature adopted for the slurry step (3) selected in the range from 60 to 95° C., in particular it proceeds with excellent yields and always reaches completion within a maximum of 48 hours from the start, at any temperature above about 70° C.; in order to obtain even faster conversion times, the slurry step (3) is preferably carried out at a temperature higher than 75° C. When said slurry step (3) is carried out at a temperature above 75° C., the conversion of sodium neridronate into the crystalline polymorphic hemihydrate form F of sodium neridronate is completed in less than 24 hours.

The successful completion of the conversion of sodium neridronate into the crystalline polymorphic hemihydrate form F of sodium neridronate is easily monitored by any analysis technique on solid crystal samples taken from the suspension in the slurry step (such as for example XRPD or FT-IR).

In any case, in any of the conditions of the process of the invention, the conversion of the starting crystals of sodium neridronate into the crystalline polymorphic hemihydrate form F of sodium neridronate occurs with very high yields, always above 80%.

Advantageously, at the end of the slurry step (3), once the completion of the conversion of the starting crystals of sodium neridronate into the crystalline polymorphic hemihydrate form F of sodium neridronate has been assessed, the suspension can be cooled down before being subjected to well-known techniques for recovery of the solid, referred to in step (4).

By way of example, step (4) may be carried out by filtration of the suspension, optionally preceded by cooling thereof, followed by washing of the filtrate, for example with water/ethanol mixtures or pure ethanol, and drying.

Preferably, the washing of the filtrate is carried out with a water:ethanol mixture in a 1:1 volume ratio, followed by a second washing with pure ethanol.

The drying is preferably carried out under a nitrogen stream, and then under vacuum.

Due to its characteristics, it is apparent that said process of preparation of the crystalline hemihydrate form F of sodium neridronate can be advantageously applied downstream of any sodium neridronate synthetic process described in the prior art, being able to convert any crystalline solid form deriving from said prior art synthetic processes into the crystalline hemihydrate form F of sodium neridronate. In particular, said process for obtaining the crystalline hemihydrate form F of sodium neridronate may be used downstream of any synthetic process known to date and employed to obtain sodium neridronate starting, for example, from neridronic acid.

In another aspect, the invention therefore also relates to a novel synthetic process for obtaining sodium neridronate comprising the following steps:
a) reacting 6-aminohexanoic acid with a mixture of phosphorous acid and methanesulfonic acid, and obtain a mixture;
b) adding phosphorus trichloride to said mixture in step (a), under stirring and at a temperature in the range from 60 to 80° C., keeping the mixture obtained under stirring at a temperature in the range from 60 to 70° C. for at least 15 hours;
c) diluting the mixture obtained in the previous step (b) with water, and heating said mixture diluted with water to a temperature in the range from 90 to 120° C. for at least 13 hours, obtaining a heated mixture;
d) cooling the heated mixture obtained from step (c) to a temperature below 75° C., and slowly adding sodium hydroxide to a pH in the range from 3 to 5, obtaining a suspension;
e) cooling the suspension obtained in step (d) to a temperature in the range from 10 to 30° C., then slowly adding ethanol to obtain the precipitation of the sodium salt of sodium neridronate in any crystalline form;
f) recovering the sodium neridronate in any crystalline form formed in the previous step (e).

Preferably the mixture of phosphorous acid and methanesulfonic acid used in step (a) is prepared by adding the methanesulfonic acid to phosphorous acid, under stirring and at a temperature in the range from 15 to 25° C., until it is completely dissolved.

Preferably said process is carried out using in step (a) a 1:1 ratio between the phosphorous acid equivalents and the 6-aminohexanoic acid equivalents.

Preferably, in step (a) said 6-aminohexanoic acid is added portionwise into the reactor containing the mixture of phosphorous acid and methanesulfonic acid.

Preferably, in step (a) said 6-aminohexanoic acid is added into the reactor containing the mixture of phosphorous acid and methanesulfonic acid at a temperature in the range from 20 to 30° C.

Preferably, the number of equivalents of phosphorus trichloride added in step (b) of the process are double the equivalents of phosphorus acid used in step (a).

Preferably, in said step (b), the reaction mixture prepared in step (a) is brought to a temperature of about 70° C. before the dropwise addition, and under stirring, of said phosphorus trichloride.

Preferably, after the addition of phosphorus trichloride in step (b), the solution is kept under stirring at a temperature in the range from 60 to 70° C. for a period of time from 18 to 30 hours, more preferably of 24 hours.

Preferably in step (c), involving contact with water, the added water causes the mixture to rapidly cool down; more preferably, the water to be added is added in two successive aliquots to better control the exothermy of the hydrolysis reaction.

Preferably, the mixture diluted with water obtained in step (c) is heated to a temperature in the range from 95 to 115° C., more preferably at the temperature of about 110° C. More preferably, said heating is kept under reflux for about 20 hours, under stirring.

Preferably, in step (d) the mixture obtained from step (c) is cooled to a temperature in the range from 60 to 75° C.; alternatively, it is cooled to room temperature.

Preferably, the sodium hydroxide in step (d) is a 30% or 50% sodium hydroxide concentrated aqueous solution.

Preferably, said sodium hydroxide in step (d) is added until the reaction mixture is brought to a pH value in the range from about 4.0 to about 5.0, more preferably from about 4.2 to about 4.6, even more preferably from about 4.4 to about 4.6.

Preferably in step (e), the reaction mixture is cooled to a temperature in the range from 15 to 25° C. and kept under stirring for a few hours, preferably for about 2-4 hours, before adding ethanol.

Preferably in step (e), the ethanol is added slowly, under stirring, over a period of time of 30-90 minutes, until thickening of the suspension.

The recovery, in step (f), of the sodium neridronate crystalline solid formed in the precipitation step (e) may be carried out by known techniques.

Preferably, it may be carried out by vacuum filtration of the solid, followed by washing with water/ethanol mixtures, preferably water/ethanol mixtures in a 1:1 volume ratio, and then by further washing with pure ethanol, then subjected to drying.

Preferably, drying may take place under a nitrogen stream and/or vacuum.

Even more preferably, a first drying under a stream of nitrogen for a few hours, preferably about 3-6 hours, may be carried out, followed by a vacuum drying at room temperature, preferably at a temperature of about 25° C., for several hours, preferably about 40-60 hours.

Said novel synthesis process of crystalline sodium neridronate made by the inventors of the present invention allows to obtain sodium neridronate in excellent yields and purity, with yields even higher than 90%, by a much simpler and more easily industrially scalable process compared to those described in the prior art.

Moreover, the inventors have noticed that only carrying out—in step (c)—the addition of water (hydrolysis) at high temperatures it is possible to obtain an effective hydrolysis and to better control the exothermy of the reaction. Furthermore, the specific way of adding ethanol—in step (e) of the process—is a further essential feature of the process, for obtaining high yields of neridronate and avoiding the contamination by considerable quantities of sodium methanesulfonate. The slow addition of ethanol at a temperature between 10 and 30° C. step, indeed, allows the solubilisation of the formed sodium methanesulfonate, which remains only as a trace contaminant, for example in the cake obtained after filtration and washing, and which is definitively easily removed in the subsequent purification steps.

Said process leads to the obtainment of crystalline polymorphic sodium neridronate, substantially in form B, which can be efficiently and rapidly submitted, with excellent conversion yields, to the process of the invention for obtaining the crystalline hemihydrate form F of sodium neridronate, usable for the preparation of stable solid oral pharmaceutical forms based on sodium neridronate.

In a third aspect thereof, accordingly, the inventors of the present invention have therefore also developed a novel process for the preparation of the novel crystalline polymorphic hemihydrate form F of sodium neridronate of the invention, starting from 6-aminohexanoic acid, characterized by comprising the following steps:

(i) carrying out the process for the preparation of sodium neridronate in any crystalline form according to steps (a) to (f) above described;

(ii) carrying out the process for the preparation of the crystalline hemihydrate form F of sodium neridronate according to steps (1) to (4) previously described.

In other words, a novel process for the preparation of the novel crystalline polymorphic hemihydrate form F of sodium neridronate of the invention starting from 6-aminohexanoic acid has been developed, characterized by comprising the following steps:

a) reacting 6-aminohexanoic acid with a mixture of phosphorous acid and methanesulfonic acid, and obtain a mixture;

b) adding phosphorus trichloride to said mixture in step (a), under stirring and at a temperature in the range from 60 to 80° C., keeping the mixture obtained under stirring at a temperature in the range from 60 to 70° C. for at least 15 hours;

c) diluting the mixture obtained in the previous step (b) with water, and heating said mixture diluted with water to a temperature in the range from 90 to 120° C. for at least 13 hours, obtaining a heated mixture;

d) cooling the heated mixture obtained from step (c) to a temperature below 75° C., and slowly adding sodium hydroxide to a pH in the range from 3 to 5, obtaining a suspension;

e) cooling the suspension obtained in step (d) to a temperature in the range from 10 to 30° C., then slowly adding ethanol to obtain the precipitation of the sodium salt of sodium neridronate in any crystalline form;

f) recovering the sodium neridronate in any crystalline form formed in the previous step (e);

1) dissolving the solid sodium neridronate in any crystalline form from step (f) in water, at a temperature in the range from 70 to 90° C., to obtain an aqueous solution of sodium neridronate;

2) adding a solvent selected from the group consisting in ethanol, 1-propanol, and 2-propanol to the aqueous solution obtained from step (1), so that the final water:solvent volume ratio is in the range from 1:0.5 to 1:1, thus obtaining a suspension;

3) placing the suspension obtained from step (2) under mechanical stirring, at a temperature in the range from 60 to 95° C.;

4) recovering the crystalline hemihydrate form F of sodium neridronate formed in the previous step (3).

In a fourth aspect thereof, the present invention further provides pharmaceutical compositions comprising the crystalline polymorphic hemihydrate form F of sodium neridronate and pharmaceutically acceptable excipients.

The term "pharmaceutically acceptable excipients" means substances normally used in the preparation of pharmaceutical compositions such as, for example, solvents, diluents, binders, disintegrants, lubricants, buffers, wetting agents, coloring agents, flavors and/or sweeteners, and any other ingredient necessary for the preparation of said compositions.

Finally, in a fifth aspect thereof, the present invention provides therapeutic uses and therapeutic methods of treatment using pharmaceutical compositions containing the polymorph crystalline hemihydrate form F of sodium neridronate.

Said therapeutic uses and therapeutic methods of treatment are preferably aimed at the treatment of musculoskeletal and calcium metabolism disorders.

More preferably, these disorders are osteoporosis, hyperparathyroidism, hypercalcemia of malignancy, osteolytic bone metastases, myositis ossificans progressiva, universal calcinosis, arthritis, neuritis, bursitis, tendinitis, Paget's disease, osteogenesis imperfecta, Complex Regional Pain Syndrome (CRPS), and other inflammatory diseases.

Suitable pharmaceutical compositions containing crystalline polymorphic hemihydrate form F of sodium neridronate according to the invention are the compositions for the preparation of medicaments to be administered orally in solid form, such as for example tablets, capsules, cachets, pills, granules and powders. Said medicaments in solid form preferably contain a unitary amount of crystalline hemihydrate form F of sodium neridronate, expressed as free neridronic acid, comprised in the range from 50 to 500 mg, more preferably comprised between 100 and 400 mg, even more preferably equal to 100 mg, 200 mg or 400 mg.

The crystalline hemihydrate form F of sodium neridronate may also be used to prepare medicaments to be administered orally in liquid form, such as solutions, suspensions, syrups, gels, emulsions, each containing an effective amount of the polymorphic hemihydrate form F of sodium neridronate.

Alternatively, the crystalline polymorphic hemihydrate form F of sodium neridronate may also be used to prepare pharmaceutical forms to be administered topically, rectally, vaginally, parenterally, nasally and by aerosol, each containing an effective amount of the crystalline polymorphic hemihydrate form F of sodium neridronate. Advantageously, said pharmaceutical forms may be pharmaceutical forms to be administered parenterally, preferably intramuscularly or intravenously, containing a unitary amount of crystalline polymorphic hemihydrate form F of sodium neridronate, expressed as free neridronic acid, comprised in the range from 50 to 500 mg, more preferably equal to 100 mg.

Preferably said pharmaceutical forms to be administered parenterally will be in the form of an aqueous solution.

The pharmaceutical compositions according to the invention may be prepared following standard methods of pharmaceutical technology.

The present invention will now be described with reference to the following examples which are provided for illustrative purposes only and should not be construed as limiting the scope of the present invention.

Example A (According to Prior Art Described in WO2008/004000). Preparation of Crystalline Polymorphic Form E of Sodium Neridronate A mixture of 6-aminohexanoic acid (20.0 g, 0.152 mol) and phosphorous acid (18.8 g, 0.229 mol) in acetonitrile (300 ml) was heated to a temperature of 60-65° C., then phosphorus trichloride (41.8 g, 0.304 mol) was slowly added under stirring. At the end of the phosphorus trichloride addition, the temperature of the reaction mixture was increased to 70-75° C., and the reaction mixture was maintained under such conditions for 9 hours. The reaction mixture was then cooled to a temperature of 60-65° C., and water (150 ml) was slowly added at this temperature. The temperature of the reaction mixture was then increased again to 95°-100° C., and the reaction mixture was maintained under these conditions for 5-6 hours. The reaction mixture was then cooled to 55-65° C., and the pH of the reaction mixture adjusted to a value of 4.4-4.8 by addition of a sodium hydroxide solution. The reaction mixture was then cooled to 25-35° C., and the aqueous layer containing the product was separated from the upper layer containing acetonitrile. After addition of acetone (80 ml) to the aqueous layer, it was cooled to 0-5° C. and maintained at this temperature for 3 hours.

The solid product was separated by filtration and then washed, first with water and then with methanol, until obtaining crystalline sodium neridronate.

The product was dried under vacuum at 45-50° C. until the loss of mass was less than 0.5% (weight/weight). 18.5 g (yield 45.6%) of crystalline sodium neridronate were obtained, which were subjected to XRPD analysis.

The XRPD analyses were performed with a X'pert PRO PANalytical instrument using Cu/K-alpha1 radiation. The instrument was equipped with an X-ray tube with line focus (tube voltage and amperage set at 40 kV and 40 mA, respectively), and equipped with a ½° anti-scatter slit, a ½° divergence slit, a 5.00 mm receiving slit, a 0.04 rad soller slit, and a RTMS X'Celerator detector. The scan was carried out between 3-40° with a step size of 0.0167°. The instrument alignment was periodically checked by means of a silica standard, and the sample was prepared by top-loading of the powder on glass sample holders.

Figure 1:
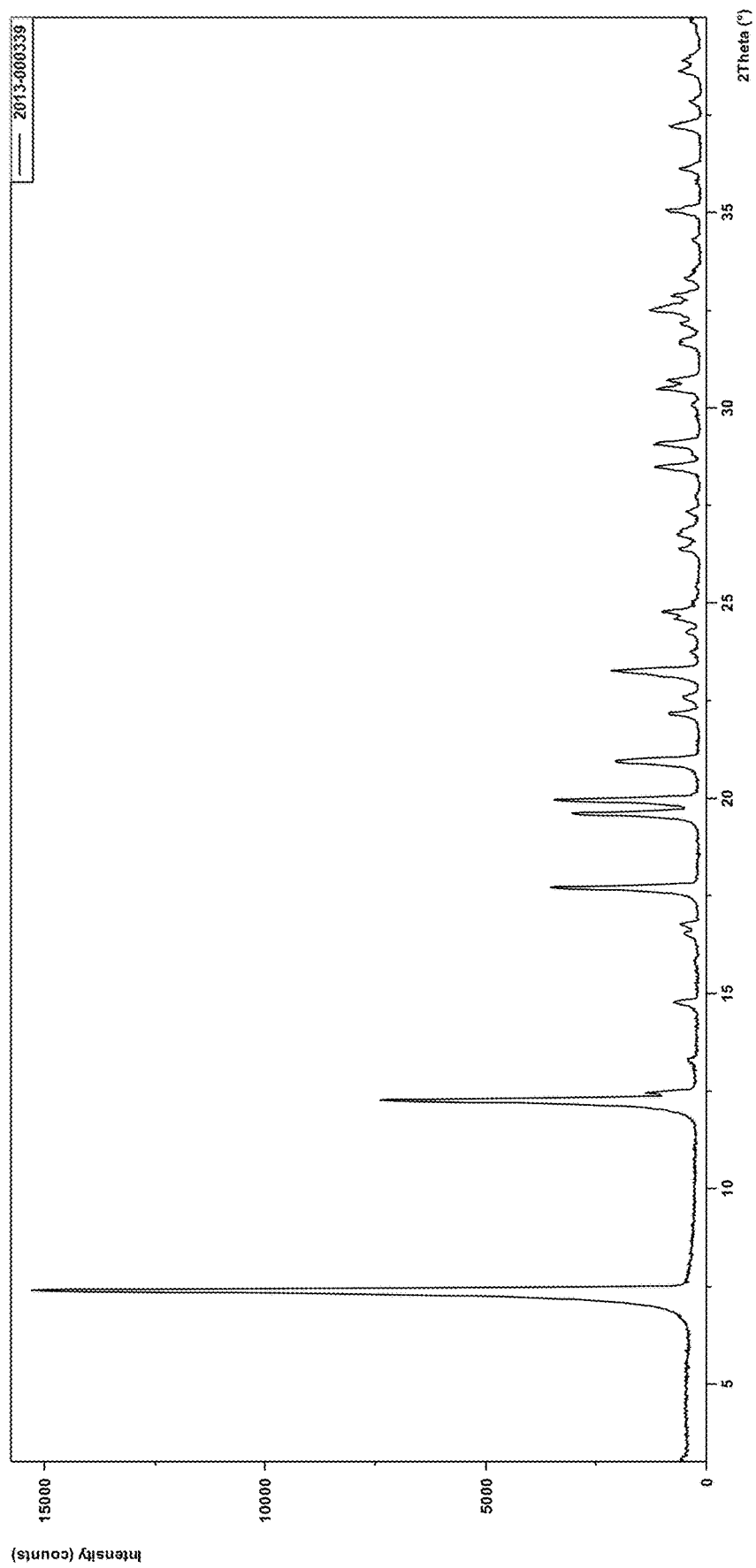
FIG. 1: XRPD of the crystalline polymorphic hemihydrate form E of sodium neridronate.

The diffractogram of the polymorphic crystalline sodium neridronate, which was designated "Form E" by the inventors of the present invention, is depicted in FIG. 1 and showed characteristic 2θ peaks at 7.43°, 12.28°, 12.47°, 17.72°, 19.62°, 19.97°, 20.990, 23.280, 28.49° e 32.49°.

Example B (According to Prior Art Described in EP0494844). Preparation of Form B of Crystalline Polymorphic Sodium Neridronate 10.5 g (6.67 mL, 76.33 mmol, 5 eq.) of phosphorus trichloride were added dropwise to a molten mixture obtained by heating 2 g (15.27 mmol) of 6-aminohexanoic acid and 7.5 g (91.6 mmol, 6 eq.) of phosphorous acid to 90° C., under stirring and under a nitrogen atmosphere, so as to maintain a moderate reflux. These conditions were maintained, also at the end of the dropwise addition of phosphorus trichloride, for about 2 hours to distill away an aliquot of excess phosphorus trichloride.

A 20% HCl solution (15.3 mL) was then cautiously added, and the solution thus obtained was then brought to reflux conditions for 6 hours; after which decolorizing activated charcoal (Darco, 50 mg) was added.

The solution was then cooled to room temperature, the activated charcoal filtrated off, and an equal volume of methanol was added under stirring. A suspension containing neridronic acid was formed.

A neutralization step was then performed by slow addition, at a temperature of 80° C., of a 30% NaOH solution (about 23 mL) directly into the aqueous methanol solution up to opalescence. The suspension was then stirred at room temperature until a large amount of white precipitate was visible.

The reaction product was collected under vacuum, washed with methanol (3×20 mL) and dried in a static oven at 50° C. for 24 hours. 3.4 g of a white solid (yield=74.6%) were recovered, which was subjected to XRPD analysis.

The XRPD analyses were performed with a X'pert PRO PANalytical instrument using Cu/K-alpha1 radiation. The instrument was equipped with an X-ray tube with line focus (tube voltage and amperage set at 40 kV and 40 mA, respectively), and equipped with a ½° anti-scatter slit, a ½° divergence slit, a 5.00 mm receiving slit, a 0.04 rad soller slit, and a RTMS X'Celerator detector. The scan was carried out between 3-40° with a step size of 0.0167°. The instrument alignment was periodically checked by means of a silica standard, and the sample was prepared by top-loading of the powder on glass sample holders.

Figure 2:
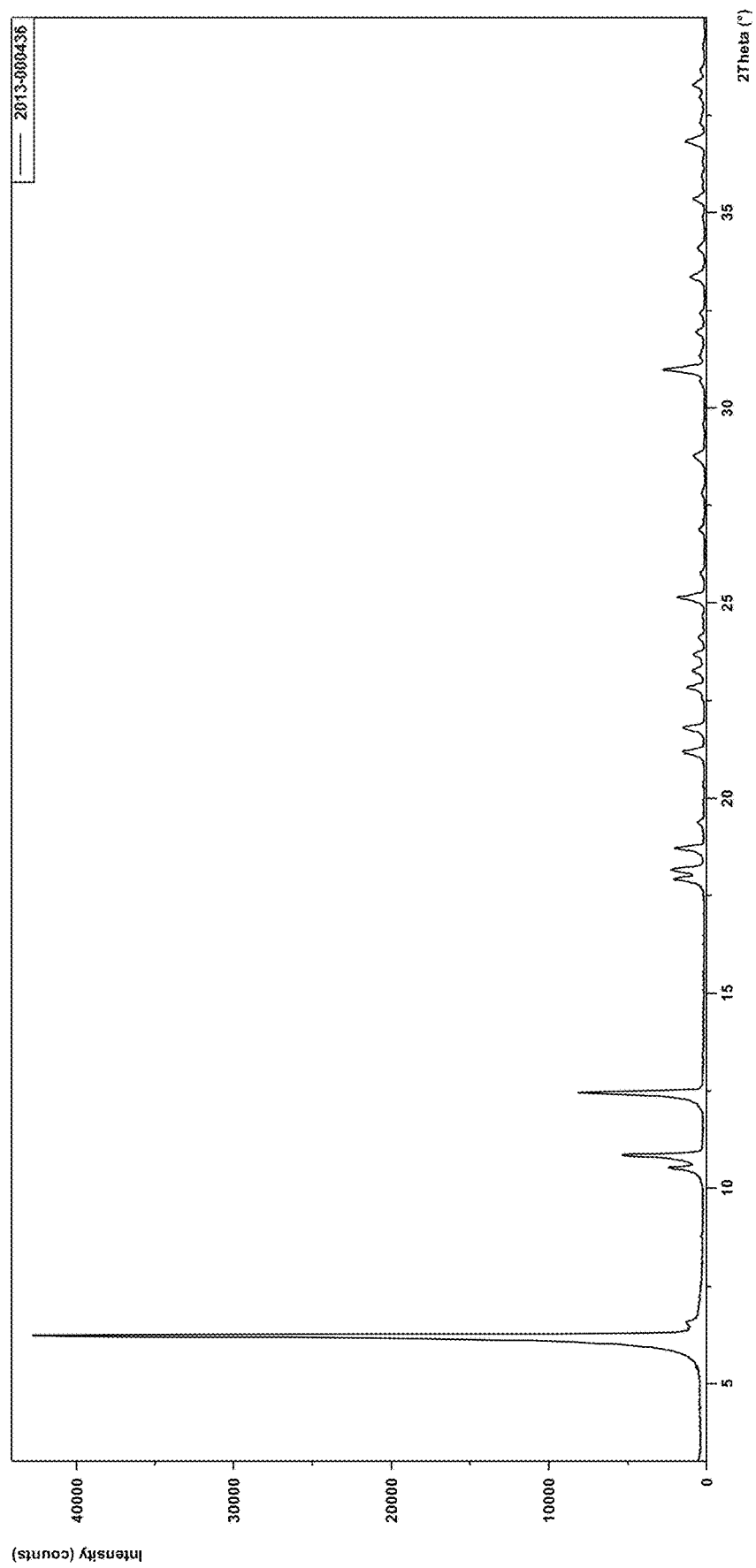
FIG. 2: XRPD of the crystalline polymorphic form B of sodium neridronate.

The diffractogram of the polymorphic crystalline sodium neridronate, which was designated "Form B" by the inventors of the present invention, is depicted in FIG. 2 and showed characteristic 2θ peaks at 6.2374°, 12.4667°, 10.8647°, 30.9783°, 10.5338°, 18.1828°, 18.7263°, 17.9257°, 25.1475° e 21.8088°.

Example 1. Preparation of Crystalline Hemihydrate Form F of Sodium Neridronate 4 g of crystalline polymorphic form B of sodium neridronate obtained in Example B were dissolved at 80° C. in 28 mL (7 vol) of water. Said solution was then filtered, and the filter and reactor rinsed with 4 mL (1 vol) of water, then added to the solution. 22 mL (5.5 vol) of ethanol (final water:ethanol volume ratio equal to about 1:0.69) were then added, and the suspension obtained was kept under stirring at 80° C., checking the progress of the process at regular intervals by XRPD check on aliquots of suspended crystals.

After maintaining these slurry conditions for about 20 hours, there were no more significant variations in the XRPD diffractograms performed on the aliquots of suspended crystals, whereby the crystalline sodium neridronate was separated, according to conventional methods (85.2% yield), and said crystalline sodium neridronate thus obtained was subjected to XRPD analysis.

The XRPD analyses were performed with a X'pert PRO PANalytical instrument using Cu/K-alpha1 radiation. The instrument was equipped with an X-ray tube with line focus (tube voltage and amperage set at 40 kV and 40 mA, respectively), and equipped with a ½° anti-scatter slit, a ½° divergence slit, a 5.00 mm receiving slit, a 0.04 rad soller slit, and a RTMS X'Celerator detector. The scan was carried out between 3-40° with a step size of 0.0167°. The instrument alignment was periodically checked by means of a silica standard, and the sample was prepared by top-loading of the powder on glass sample holders.

The diffractogram of the polymorphic crystalline sodium neridronate, which was designated "Form F" by the inventors of the present invention, is depicted in FIG. 3 and showed characteristic 2θ peaks at 6.51°, 12.02°, 16.51°, 16.66°, 20.80°, 22.21°, 25.30°, 27.65°, 30.05° e 31.87°.

According to experimental evidence, therefore, the process of the invention allowed to obtain a completely novel form of polymorphic crystalline sodium neridronate (Form F).

The diffractograms of the polymorphic sodium neridronate form E of Example A and FIG. 1, form B of Example B and FIG. 2 and form F of Example 1 e FIG. 3, clearly highlight the uniqueness of each XRPD spectrum, and therefore the fact that the three crystalline forms, form F, E and B, are three different polymorphic forms of sodium neridronate, perfectly distinguishable one from the other.

Example 2. Single-Crystal X-Ray Diffraction (SC-XRD) of Form F

A crystal of hemihydrate form F of sodium neridronate, with approximate dimensions of 0.366×0.195×0.120 mm$^3$, was mounted on a glass fiber in a random orientation. Data on the crystal were collected at room temperature on an Oxford Xcalibur S X-ray diffractor, Mo-k radiation, λ=0.71073 Å with a graphite monochromator and a CCD Sapphire detector.

The cell constants and the orientation matrix for data collection were obtained by "least-square refinement" using setting angles of 1288 reflections in the range 2.77°<θ<29.60°.

The space group was determined using the SGRAL program, and resulted to be P21/c.

The structure was resolved using direct methods and refined by "full-matrix least-squares" on F2 using SHELX97 program.

An XRPD pattern calculated for the Cu radiation was generated using Mercury software, version 2.2, and atomic coordinates, space group, and the unitary cell parameter deriving from the single-crystal data. The Mercury program was used for graphical representation of the results.

From the measurements carried out, it was found that the sample consisting of the crystal of hemihydrate form F of sodium neridronate crystallizes in a monoclinic system having the cell parameters shown in the following Table 1:

TABLE 1

| MONOCLINIC SYSTEM | |
| --- | --- |
| a = 14.3749 (3) Å | α: 90° |
| b = 8.76600 (10) Å | β: 109.339 (2)° |
| c = 21.2927 (4) Å | γ: 90° |
| Volume = 2531.71 (8) Å$^3$ | Space group: P21/c |
| Z: 8 | T: 293 (2) K |

Figure 4:
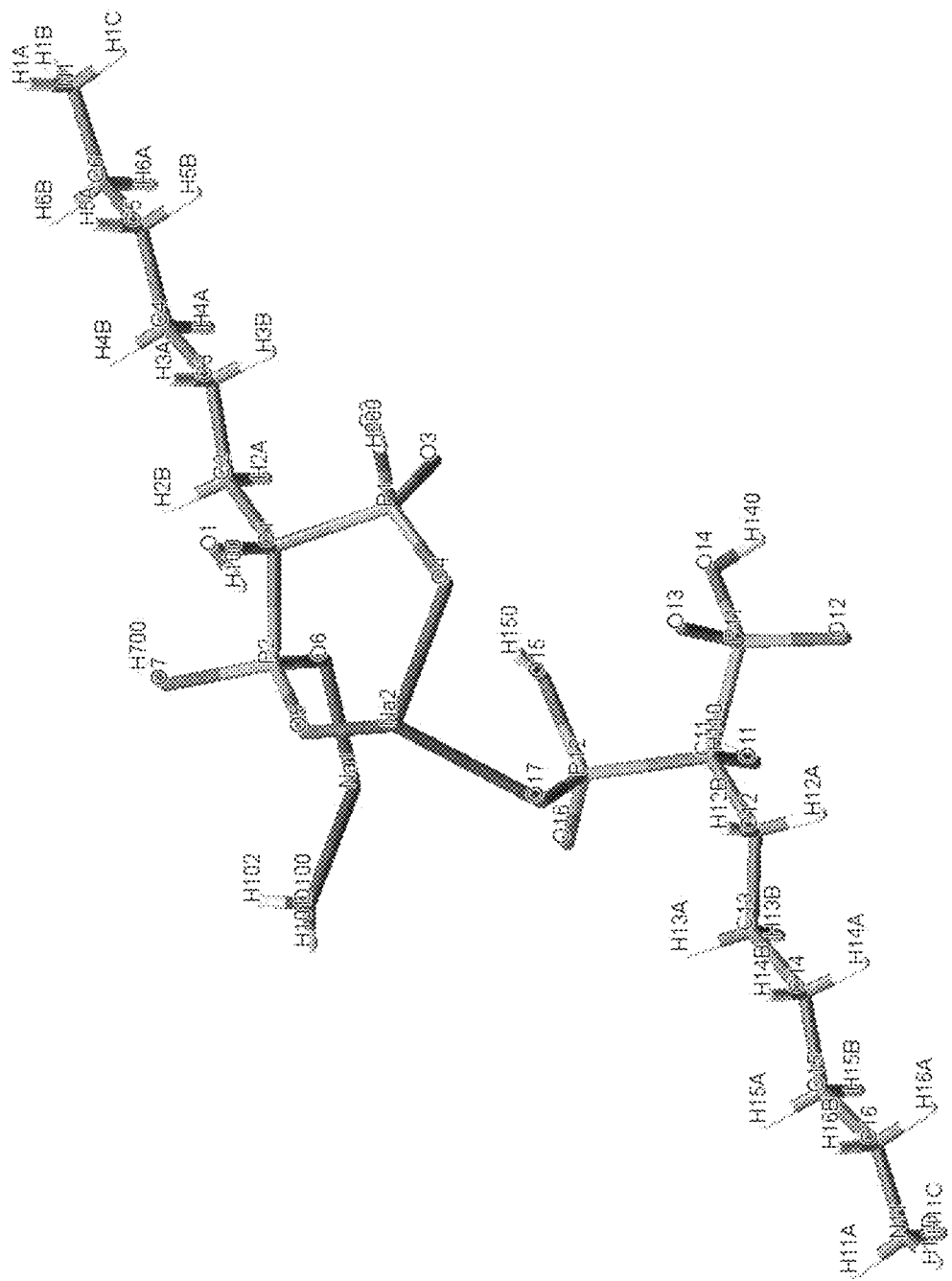
FIG. 4: Molecular structure design of crystalline hemihydrate form F of sodium neridronate.

The molecular structure design of the hemihydrate form F of sodium neridronate, obtained with the aid of the Mercury program version 2.2, is shown in FIG. 4: the asymmetric unit consists of two molecules of sodium neridronate and one molecule of water. The form F is, therefore, a hemihydrate form.

Example 3. Fourier-Transform Infrared Spectroscopy FT-IR

The infrared spectra were acquired using a Nicolet FT-IR 6700 Thermo Fisher type Fourier Transform Infrared Spectrometer.

The infrared spectra of the polymorphs F, E and B are shown in FIGS. 5, 6 and 7, respectively, and highlight and confirm the completely different nature of the three crystalline forms.

Example 4. Hygroscopicity Study by Dynamic Vapor Sorption (DVS)

The Hygroscopicity study was carried out on samples of polymorphic crystalline forms F, B and E of sodium neridronate by measuring the humidity absorption kinetics, in a range of relative humidity (RH %) comprised between 0 and 90%, at the temperature of 25° C.

Figure 8A:
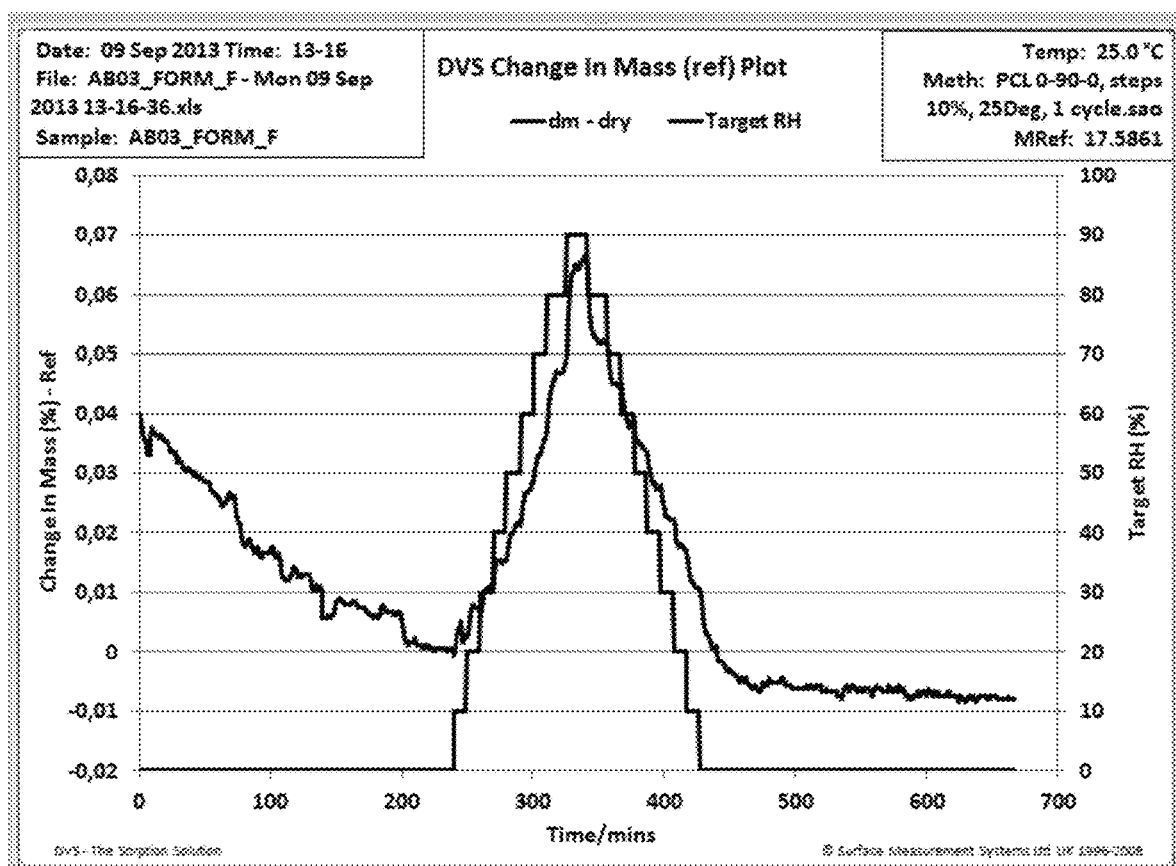
FIG. 8a-8b-8c: Hygroscopicity study carried out by means of Dynamic Vapor Sorption (DVS) analysis. Kinetics of humidity absorption of crystalline hemihydrate form F of sodium neridronate (FIG. 8a), form E (FIG. 8b) and form B (FIG. 8c).

The crystalline hemihydrate form F showed a hydrophobic behavior, without any appreciable mass variation, even under the most extreme experimental conditions, i.e. in the presence of 90% relative humidity (RH) at a temperature of 25° C., as it is apparent from the graph in FIG. 8a.

Figure 8B:
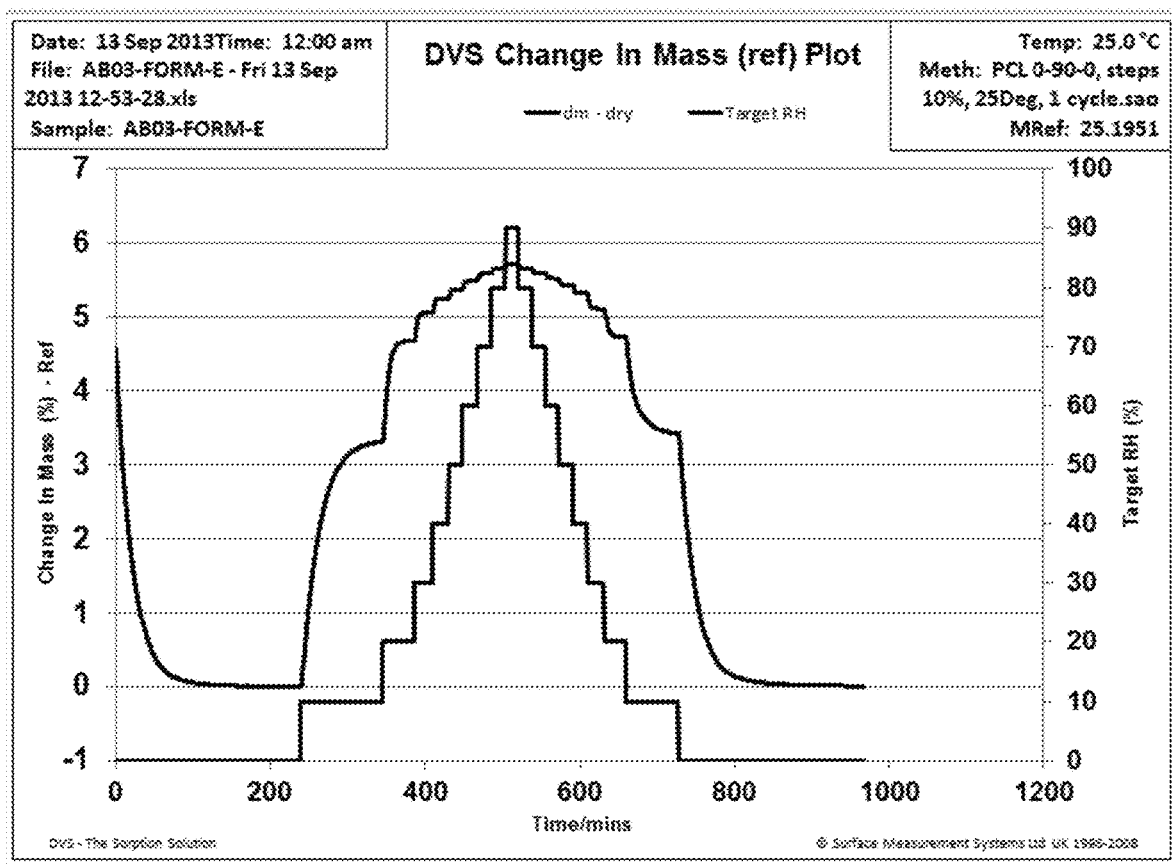
Figure 8C:
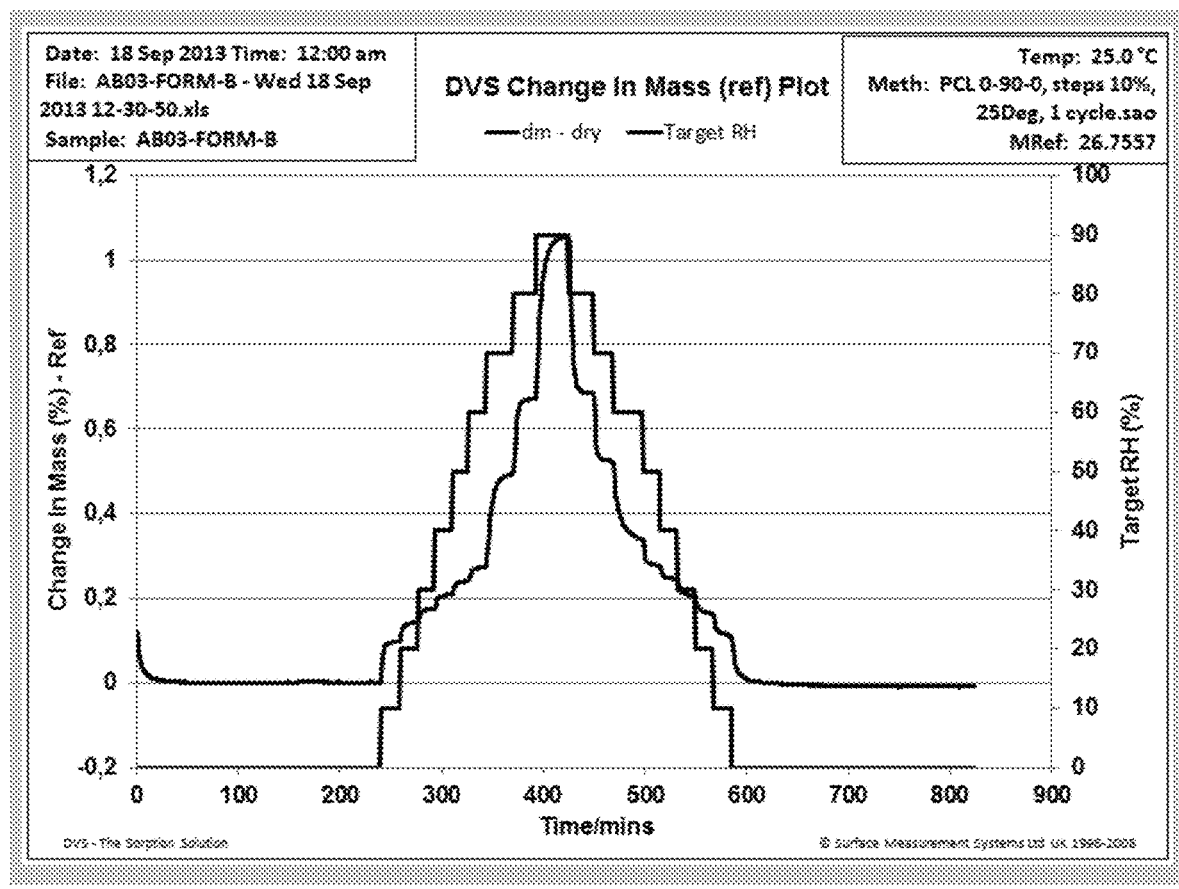

Conversely, forms E and B, in the same conditions of 90% relative humidity (RH) and a temperature of 25° C. (graphs in FIGS. 8b and 8c, respectively) showed a hydrophilic behavior, with a mass variation of about 1% and about 5%, respectively.

Polymorphic crystalline forms B and E of sodium neridronate have been therefore shown to be hygroscopic in especially humid environment, and therefore not usable in the preparation of solid oral forms.

Example 5. Stability Study

The stability study was carried out on samples of crystalline polymorphic forms B, E, and the hemihydrate form F of sodium neridronate, stored in an environment characterized by 75% relative humidity (RH) and a temperature of 40° C.

The observation of the sample stability lasted for a period of eight weeks, during which once a week, and weekly, an aliquot was taken from each sample and subjected to XRD analysis to observe any possible crystalline changes of the various samples over time.

Figure 9A:
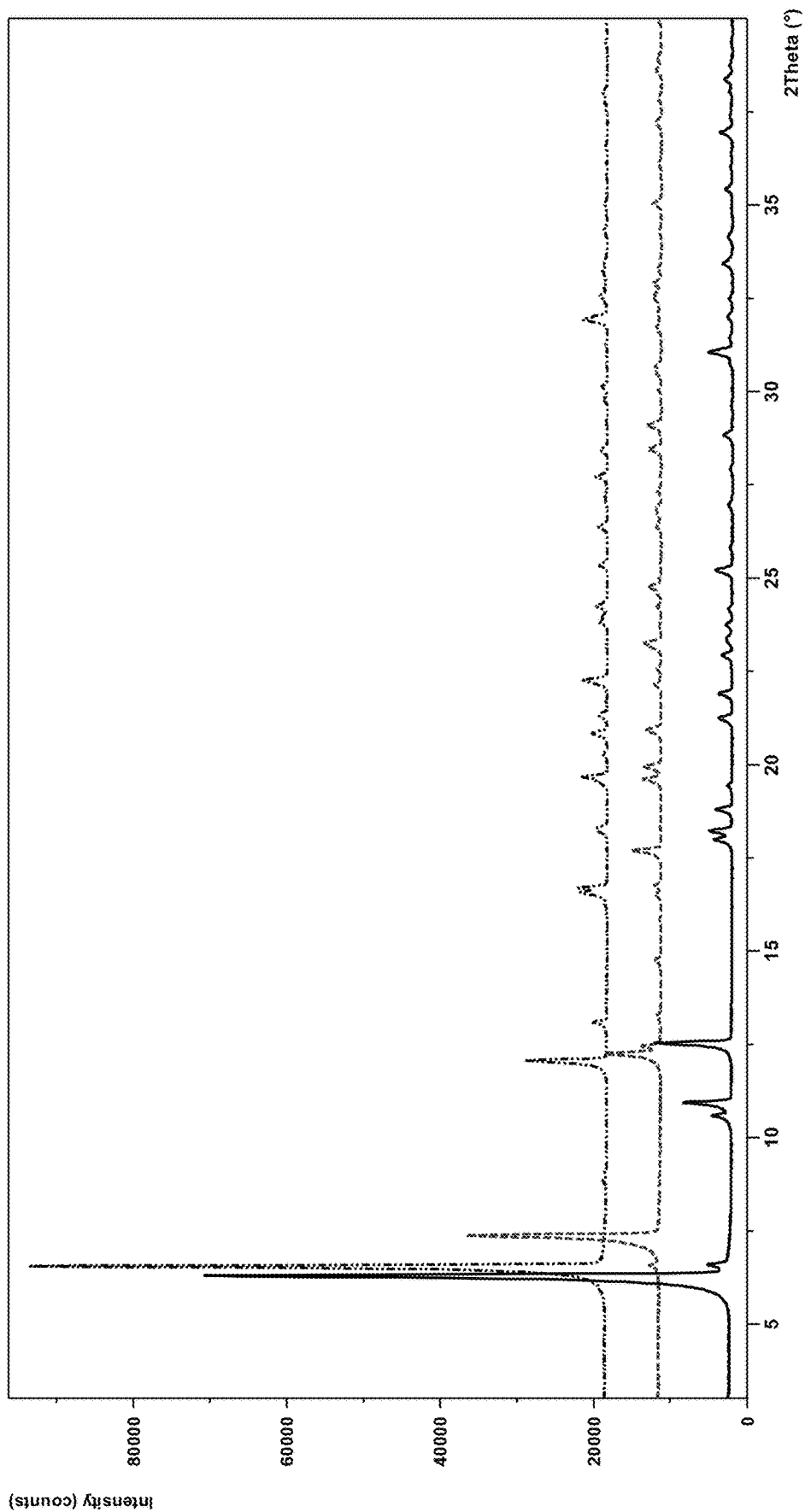
FIG. 9a-9b-9c: Stability study monitored by XRPD: diffractograms of crystalline hemihydrate form F of sodium neridronate (top dashed line), form E (middle dotted line), and form B (bottom solid line) after 1 week (FIG. 9a), 7 weeks (FIG. 9b), and 8 weeks (FIG. 9c) of conditioning at 40° C. and 75% RH.
Figure 9B:
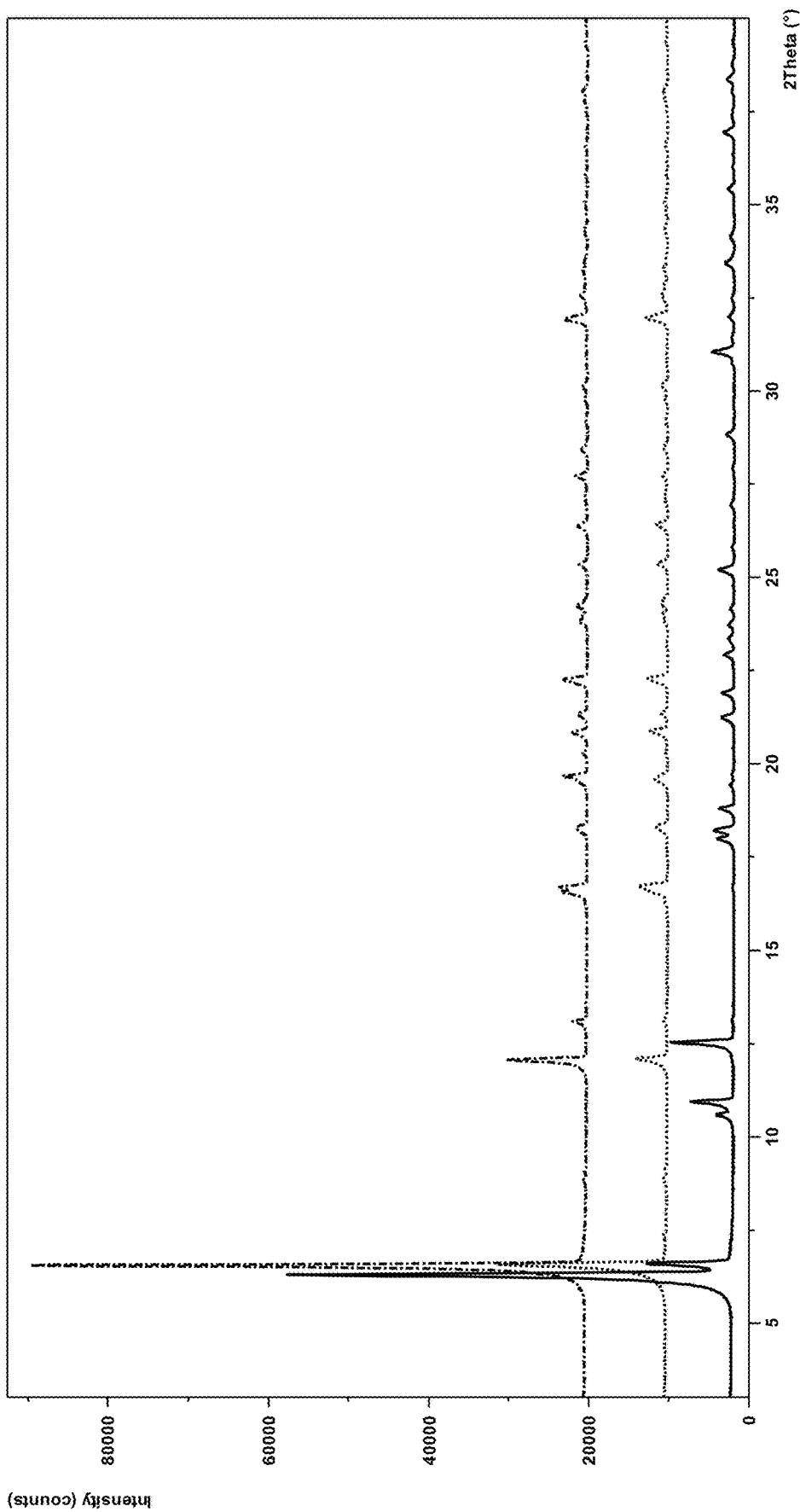
Figure 9C:
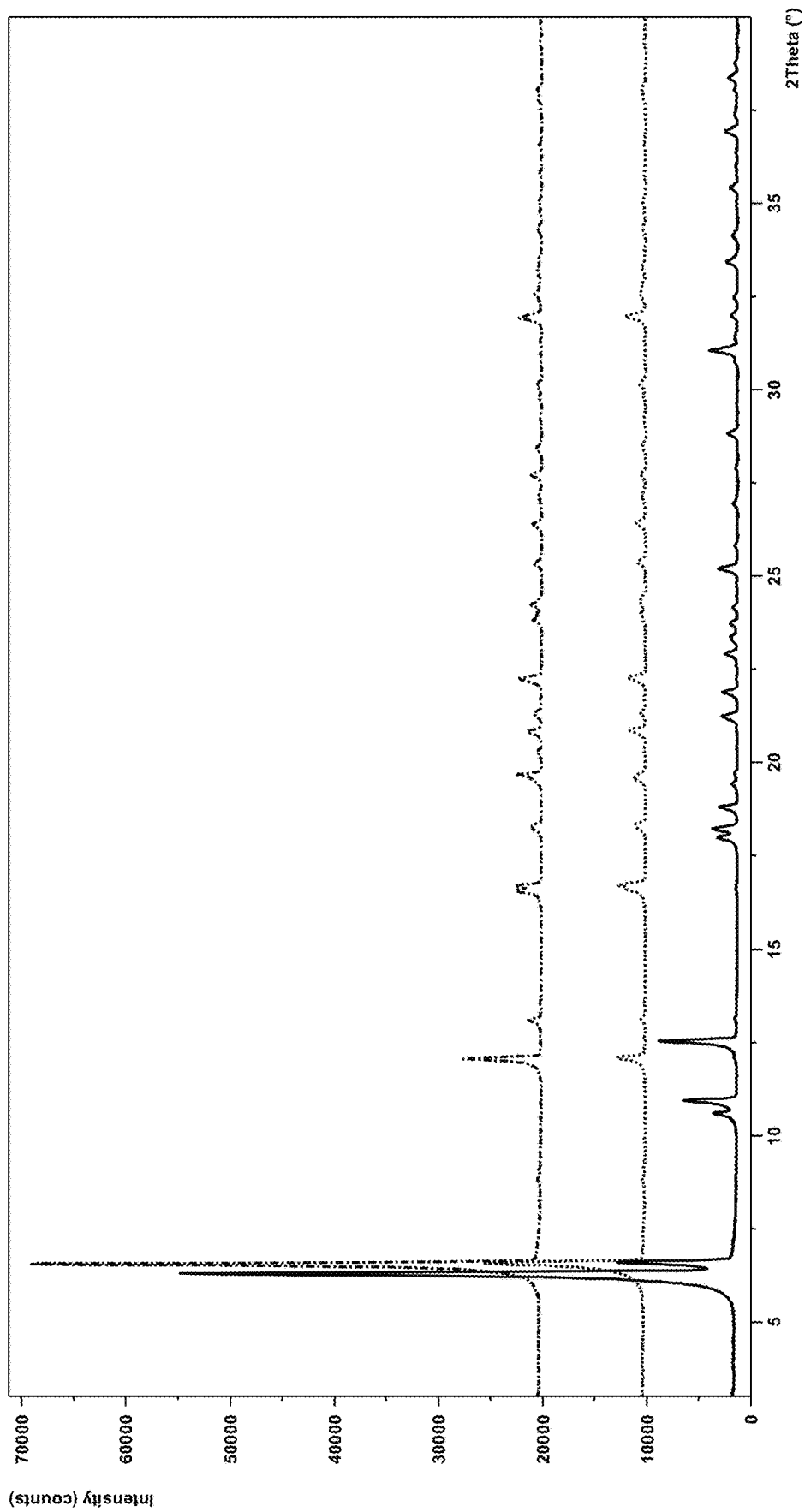

XRD analyses revealed that the crystalline polymorphic forms B and E of sodium neridronate are not stable over time and begin to convert into the crystalline hemihydrate form F already after a week. In particular, after seven weeks of observation, the crystalline polymorphic form E of sodium neridronate had completely converted into the crystalline hemihydrate form F, while the crystalline polymorphic form B of sodium neridronate had only partially converted at the end of the observation period, resulting in a sample consisting of a mixture of crystalline polymorphic form B and crystalline polymorphic hemihydrate form F. In contrast, the sample of crystalline polymorphic hemihydrate form F demonstrated to be stable even after eight weeks conditioning. The diffractometric patterns of the samples after 1 and after 7 weeks conditioning are reported in FIGS. 9a e 9b, as well as in FIG. 9c, at the end of the observation period, after 8 weeks conditioning.

Example 6. Thermodynamic Solubility Test

Considering the excellent performances of the crystalline polymorphic hemihydrate form F of sodium neridronate in terms of stability and hygroscopicity, and having therefore confirmed its possible use as raw material for the production of solid pharmaceutical forms, the crystalline polymorphic hemihydrate form F of sodium neridronate was characterized also in terms of thermodynamic solubility.

For this purpose, a dissolution test was carried out in a buffer solution at pH 7.4. The thermodynamic solubility evaluation was performed leaving the sample in the buffer solution, under magnetic stirring at about 500 rpm, for a period of 24 hours, at a temperature of 37° C.

Under the experimental conditions, the thermodynamic solubility of crystalline polymorphic hemihydrate form F of sodium neridronate was equal to 93.71 mg/ml, a perfectly acceptable value in case of use of this crystalline polymorphic hemihydrate form F in the preparation of solid oral forms.

The obtained thermodynamic solubility value for the crystalline hemihydrate form F is also fully comparable to the solubility value obtainable for form B (92.97 mg/ml), which has always been used in the preparation of injectable compositions. Therefore, this makes the crystalline hemihydrate form F usable, likewise to form B, in the preparation of compositions for injectable pharmaceutical forms as well.

Example 7. Check of the Slurry Step Dependence on Temperature in the Obtainment of the Crystalline Hemihydrate Form F of Sodium Neridronate In this experiment we wanted to check the dependence of the process for obtaining the crystalline hemihydrate form F of sodium neridronate on the slurry conditions adopted, with particular reference to the slurry temperature.

The process was carried out starting from the crystalline form B of sodium neridronate, obtainable from synthetic processes of the prior art, using an experimental apparatus consisting of a 200 mL jacketed reactor connected to a cooling system which operated the temperature control.

Each reaction mixture was kept under mechanical stirring at a rate of 100-102 rpm, and each reactor was equipped with a steam condenser.

The experiments were performed according to the procedure described below. About 5 grams of crystalline form B of sodium neridronate, obtained from synthetic processes of the prior art, were weighed and transferred into the reactor containing a mixture of water and ethanol in the desired quantities and proportions, as indicated in detail in the following Table 2.

This suspension was then subjected to stirring at a rate of 100-102 rpm, and heated until reaching the desired temperature comprised in the range from 50 to 85° C., and maintained in such slurry conditions for the entire duration of the experiment, i.e. up to complete conversion of the various crystalline forms into form F.

To check the successful conversion into form F, samples of the above-described mixture were taken at regular intervals and analyzed by XRPD, until the complete conversion of the suspension crystal into the hemihydrate form F was observed.

Once said conversion was obtained, the mixture was cooled to room temperature and the dispersed solid was collected by vacuum filtration, washed with about 5 mL of a 1:1 (vol:vol) water and ethanol mixture, and then with about 20 mL of ethanol alone.

The solid was subsequently dried at a temperature of 40° C. for about 8-20 hours, weighed, and finally analyzed by XRPD.

The results of the experiments carried out are listed in the same Table 2.

TABLE 2

| Temperature (° C.) | Water Volume (mL) | Ethanol Volume (mL) | Water:Ethanol Ratio (volume:volume) | Conversion Time to Form F (hours) | Yield % |
|---|---|---|---|---|---|
| 50 | 37.5 | 32.5 | 1:0.87 | 163 | 84.6 |
| 63 | 37.5 | 32.5 | 1:0.87 | 80 | 85.7 |
| 70 | 37.5 | 32.5 | 1:0.87 | 46 | 86.5 |
| 77 | 37.5 | 32.5 | 1:0.87 | 22 | 86.0 |
| 85 | 37.5 | 32.5 | 1:0.87 | 10 | 80.2 |

As can be seen from the results of the experiments carried out and represented in the above Table 2, the conversion into crystalline polymorph hemihydrate F is complete in all the process conditions tested, and in particular in all the temperature conditions used for the slurry step, however, in the case of temperatures below about 60° C., conversion times were so long not to be practically feasible for their implementation at an industrial level. Conversely, operating temperatures above 70° C. were absolutely practicable, providing high yields of product in relatively short periods, within 24 hours, and even well within 12 hours for even higher temperatures.

Example 8. Check of the Slurry Step Dependence on Compositional Ranges of the Water/Ethanol Mixture in the Obtainment of Crystalline Hemihydrate Form F of Sodium Neridronate In this experiment we wanted to check the dependence of the process for obtaining the crystalline hemihydrate form F of sodium neridronate on the slurry conditions adopted, with particular reference to the compositional ranges of the water/ethanol mixture used.

The process was carried out starting from the crystalline form B of sodium neridronate, obtainable from synthetic processes of the prior art, using an experimental apparatus consisting of a 200 mL jacketed reactor connected to a cooling system which operated the temperature control.

Each reaction mixture was kept under mechanical stirring at a rate of 100-102 rpm, and each reactor was equipped with a steam condenser.

The experiments were performed according to the procedure described below.

About 5 grams of crystalline form B of sodium neridronate, obtained from synthetic processes of the prior art, were weighed and transferred into the reactor containing a mixture of water and ethanol in the volume ratios listed in the following Table 3.

TABLE 3

| Water Volume (mL) | Ethanol Volume (mL) | Water:Ethanol Ratio (volume:volume) |
|---|---|---|
| 37.5 | 12.5 | 1:0.33 |
| 37.5 | 17.5 | 1:0.47 |
| 37.5 | 22.5 | 1:0.60 |
| 37.5 | 27.5 | 1:0.73 |
| 37.5 | 32.5 | 1:0.87 |
| 37.5 | 37.5 | 1:1.00 |
| 37.5 | 42.5 | 1:1.13 |

This suspension was then subjected to stirring at a rate of 100-102 rpm, heated until reaching a temperature of about 70° C., and maintained in such slurry conditions for the entire duration of the experiment, i.e. until complete conversion of the various crystalline forms into the hemihydrate form F.

To check the successful conversion into the crystalline hemihydrate form F, samples of the above described mixture were taken at regular intervals and analyzed by XRPD, until the complete conversion of the suspended crystal into the hemihydrate form F was observed.

Once said conversion was obtained, the mixture was cooled to reach room temperature and the dispersed solid was collected by vacuum filtration, washed with about 5 mL of a 1:1 water:ethanol mixture, and then with about 20 mL of ethanol alone.

The solid was subsequently dried at a temperature of 40° C. for about 8-20 hours, weighed and finally analyzed by XRPD.

This experimentation showed that, for water:ethanol volume ratios higher than about 1:0.50, the yield of the process dropped significantly, making the process de facto not very advantageous or economically unsustainable at an industrial level.

Values of said ratio lower than 1:1.00, on the other hand, involved very long conversion times, equally not practicable at an industrial level.

The experimentation therefore showed, under the tested conditions, that the compositional ranges of the water/ethanol mixture to be used so that the slurry could effectively lead to the effective conversion of the form B into the hemihydrate form F, were comprised between about 1:0.50 and about 1:1.00.

The most advantageous conditions, among those tested, which minimized the ethanol content needed and nevertheless obtained high yields of crystalline polymorph F, resulted to be those wherein the water:ethanol volume ratio was comprised between about 1:0.50 and 1:0.80.

Example 9. Check of the Robustness of the Process for Obtaining the Crystalline Hemihydrate Form F of Sodium Neridronate In this experiment, we wanted to check the robustness of the process for obtaining the crystalline hemihydrate form F of sodium neridronate, in relation to both the type of starting polymorph used and the slurry conditions adopted, in particular with reference to the slurry temperature and the composition of the water/ethanol mixture used.

The process was therefore carried out starting from the various crystalline forms E and B obtainable from the synthetic processes of the prior art, using an experimental apparatus consisting of a 200 mL jacketed reactor connected to a cooling system which operated the temperature control.

Each reaction mixture was kept under mechanical stirring at a rate of 100-102 rpm, and each reactor was equipped with a steam condenser.

The experiments were performed according to the procedure described below. About 5 grams of sodium neridronate in crystalline form (B and E), obtained from synthetic processes of the prior art, were weighed and transferred into the reactor containing a mixture of water and ethanol in the desired quantities and proportions, as indicated in detail in the following Table 4.

Such liquid mixture was then subjected to stirring at a rate of 100-102 rpm, and heated until reaching the desired temperature, comprised in the range from 70 to 85° C., and maintained in such slurry conditions for the entire duration of the experiment, i.e. up to complete conversion of the various crystalline forms into the crystalline form F.

To check the successful conversion into the crystalline hemihydrate form F, samples of the above-described mixture were taken at regular intervals and analyzed by XRPD, until the complete conversion of the suspension crystal into the crystalline hemihydrate form F was observed.

Once said conversion was obtained, the mixture was cooled to room temperature and the dispersed solid was collected by vacuum filtration, washed with about 5 mL of a 1:1 (vol:vol) water and ethanol mixture, and then with about 20 mL of ethanol alone.

The solid was subsequently dried at a temperature of 40° C. for about 8-20 hours, weighed, and finally analyzed by XRPD.

The results of the experiments carried out are listed in the same Table 4.

TABLE 4

| Polymorph | Temperature (° C.) | Water Volume (mL) | Ethanol Volume (mL) | Water:Ethanol Ratio (volume:volume) | Conversion time into form F (hours) | Yield % |
|---|---|---|---|---|---|---|
| B | 70 | 37.5 | 22.5 | 1:0.6 | 29 | 84.5 |
| B | 70 | 37.5 | 27.5 | 1:0.73 | 29 | 83.7 |
| B | 70 | 37.5 | 32.5 | 1:0.87 | 46 | 86.5 |
| B | 77 | 37.5 | 22.5 | 1:0.6 | 22 | 82.5 |
| B | 77 | 37.5 | 27.5 | 1:0.73 | 22 | 85.2 |
| B | 77 | 37.5 | 32.5 | 1:0.87 | 22 | 86.0 |
| B | 85 | 37.5 | 22.5 | 1:0.6 | 10 | 93.9 |
| B | 85 | 37.5 | 27.5 | 1:0.73 | 7 | 86.8 |
| B | 85 | 37.5 | 32.5 | 1:0.87 | 10 | 80.2 |
| E | 70 | 37.5 | 22.5 | 1:0.6 | 24 | 89.0 |

TABLE 4-continued

| Polymorph | Temperature (° C.) | Water Volume (mL) | Ethanol Volume (mL) | Water:Ethanol Ratio (volume:volume) | Conversion time into form F (hours) | Yield % |
|---|---|---|---|---|---|---|
| E | 70 | 37.5 | 27.5 | 1:0.73 | 6 | 91.7 |
| E | 70 | 37.5 | 32.5 | 1:0.87 | 24 | 89.5 |
| E | 77 | 37.5 | 22.5 | 1:0.6 | 22 | 82.3 |
| E | 77 | 37.5 | 27.5 | 1:0.73 | 22 | 88.5 |
| E | 77 | 37.5 | 32.5 | 1:0.87 | 5 | 89.1 |
| E | 85 | 37.5 | 22.5 | 1:0.6 | 2.5 | 93.0 |
| E | 85 | 37.5 | 27.5 | 1:0.73 | 2.5 | 88.7 |
| E | 85 | 37.5 | 32.5 | 1:0.87 | 2.5 | 88.8 |

Observing the results of the experiments carried out, summarized in Table 4, for both the crystalline forms B and E the conversion time tends to decrease with increasing temperature. For temperatures above about 77° C., complete conversions were achieved within the first 24 hours of slurry.

Within the compositional range of the ethanol/water mixture tested, influence of the composition of the slurry mixture itself on the conversion into the crystalline hemihydrate form F was instead less influent. This suggests the possibility of adopting compositions containing lower amounts of ethanol for the benefit of greater quantities of water.

In all the operating conditions tested, the yields nevertheless resulted to be always very high and always above 80%.

As it is apparent from the results listed in the above Table 4, the process of the invention is a robust, efficient and reproducible process, which allows to rapidly obtain the crystalline hemihydrate form F of sodium neridronate, operating under conditions easily obtainable at an industrial level, and therefore at low cost, with relatively low temperatures and the use of water-based reaction mixtures with low environmental impact.

Example 10. Preparation of Crystalline Polymorphic Hemihydrate Form F of Sodium Neridronate Starting from 6-Aminohexanoic Acid 1.25 g (15.24 mmol, 1 eq.) of phosphorous acid were introduced into the reactor, into which 3.03 mL (4 vol) of methanesulfonic acid were added. The mixture was kept under stirring at room temperature until complete dissolution of the acid. 2 g (15.24 mmol) of 6-aminohexanoic acid were then added, and the reaction mixture heated to about 70° C., then 2.66 mL (30.48 mmol, 2 eq.) of phosphorus trichloride were cautiously added dropwise, and the reaction mixture thus obtained was kept under stirring for 24 hours.

After 24 hours, the reaction mixture was rapidly cooled with 7.5 mL of water (10 vol) and then heated again to about 110° C., under reflux and constant stirring, for about 20 hours.

Then, the mixture was cooled again to room temperature, and a 30% sodium hydroxide solution was added. When the pH reached the value of about 2, a copious precipitation of a white solid was observed, which was redissolved by further addition of about 200 mL of water, thus obtaining a clear solution. The pH was then adjusted to the range of about 4.2-4.6, and the solution was allowed to cool to room temperature.

Absolute ethanol (1 L, 5 vol) was then added, and the mixture kept under stirring until a very thick suspension was obtained.

The product was then isolated by vacuum filtration, washed with a water/ethanol mixture (1:1, 8 vol) and ethanol (3 vol). The white solid thus obtained was then dried under a nitrogen stream for 4 hours, then dried at a temperature of 25° C. under vacuum for 60 hours. The sodium neridronate thus obtained (4.14 g, 85.5% yield) was checked by XRPD analysis, and its crystallographic nature of form B polymorph was confirmed.

4 g of said polymorphic form B of sodium neridronate were then dissolved at 90° C. in 28 mL (7 vol) of water. This solution was then filtered, and the filter and reactor were rinsed with 2 mL (0.5 vol) of water, then added to the solution. 22 mL (5.5 vol) of ethanol were then added, and the cloudy mixture obtained was kept under stirring at 70° C., checking the progress of the process of polymorph conversion at regular intervals by XRPD check on on aliquots of the suspended crystals. After about 45 hours maintenance under these slurry conditions, the polymorph B resulted to be almost completely converted into the crystalline polymorph hemihydrate F, which was then isolated, according to conventional methods, with 84.1% yield.

Example 11. Pharmaceutical Compositions of Crystalline Polymorphic Hemihydrate Form F of Sodium Neridronate for the Preparation of Pharmaceutical Forms for Oral Use in the Form of a Capsule In order to produce solid pharmaceutical compositions, which can be administered in the form of a capsule, the crystalline polymorphic hemihydrate form F of sodium neridronate was mixed with suitable excipients. Specifically, three types of composition were made, designated as composition A, B and C, containing a unitary dosage of crystalline polymorphic hemihydrate form F of sodium neridronate of about 100, 200 and 400 mg per capsule (expressed as free neridronic acid), respectively.

The amounts of excipients contained in each capsule are listed for each composition A, B and C, in the following Tables 5-7:

TABLE 5

Composition A.

| Component | Unitary Amount |
|---|---|
| Crystalline polymorphic hemihydrate form F of sodium neridronate | 111.18 mg (corresponding to about 100 mg of free neridronic acid) |
| Magnesium Stearate | 1.50 mg |
| Talc | 15.0 mg |
| Colloidal silica | 0.50 mg |

TABLE 6

| Composition B. | |
|---|---|
| Component | Unitary Amount |
| Crystalline polymorphic hemihydrate form F of sodium neridronate | 222.36 mg (corresponding to about 200 mg of free neridronic acid) |
| Magnesium Stearate | 3.00 mg |
| Talc | 30.0 mg |
| Colloidal silica | 1.0 mg |

TABLE 7

| Composition C. | |
|---|---|
| Component | Unitary Amount |
| Crystalline polymorphic hemihydrate form F of sodium neridronate | 444.72 mg (corresponding to about 400 mg of free neridronic acid) |
| Magnesium Stearate | 6.00 mg |
| Talc | 60.0 mg |
| Colloidal silica | 2 mg |

The bulk of each composition A, B and C was prepared, in the desired amounts and respecting the weight ratios listed in Tables 5-7, by first mixing the crystalline form F of sodium neridronate with talc and colloidal silica, and adding magnesium stearate to the mixture thus obtained. After further mixing, such compositions were partitioned in capsules.

Example 12. Pharmaceutical Compositions of Crystalline Polymorphic Hemihydrate Form F of Sodium Neridronate for the Preparation of Pharmaceutical Forms for Oral Use in the Form of a Tablet In order to produce solid pharmaceutical compositions, which can be administered in the form of a tablet, the crystalline polymorphic hemihydrate form F of sodium neridronate was mixed with suitable excipients. Specifically, two types of composition were made, designated as composition D and E, containing a unitary dosage of crystalline polymorphic hemihydrate form F of sodium neridronate of about 100 and about 200 mg per tablet (expressed as free neridronic acid), respectively.

The amounts of excipients contained in each tablet are listed for each composition D and E, in the following Tables 8-9:

TABLE 8

| Composition D. | |
|---|---|
| Component | Unitary amount |
| Crystalline polymorphic hemihydrate form F of sodium neridronate | 111.18 mg (corresponding to about 100 mg of free neridronic acid) |
| Polyvinylpyrrolidone | 3.00 mg |
| Microcrystalline cellulose | 29.50 mg |
| Croscarmellose | 3.00 mg |
| Talc | 10.00 mg |
| Magnesium Stearate | 1.50 mg |

TABLE 9

| Composition E. | |
|---|---|
| Component | Unitary amount |
| Crystalline polymorphic hemihydrate form F of sodium neridronate | 222.36 mg (corresponding to about 200 mg of free neridronic acid) |
| Polyvinylpyrrolidone | 6.00 mg |
| Microcrystalline cellulose | 59.00 mg |
| Croscarmellose | 6.00 mg |
| Talc | 20.0 mg |
| Magnesium Stearate | 3.0 mg |

The bulk of each composition D and E was prepared, in the desired amounts and respecting the weight ratios listed in the Tables 8-9, according to the following method.

Polyvinylpyrrolidone was dissolved in purified water (disposable solvent) so as to prepare a binding solution. This binding solution was then used to prepare a mixture consisting of crystalline polymorphic hemihydrate form F of sodium neridronate and microcrystalline cellulose. The mixture was then subjected to extrusion, drying in a fluid bed and sieving of the granulate thus obtained. Subsequently, croscarmellose, talc and magnesium stearate were added to the granulate by mixing in a fluid bed. The final mixture thus obtained was finally compressed.

Example 13. Pharmaceutical Composition of Crystalline Polymorphic Hemihydrate Form F of Sodium Neridronate for the Preparation of Pharmaceutical Forms for Oral Use in the Form of a Filmed Tablet In order to produce a solid pharmaceutical composition, which can be administered in the form of a filmed tablet, the crystalline polymorphic hemihydrate form F of sodium neridronate was mixed with suitable excipients.

The composition made, designated as composition F, contained a unitary dosage of crystalline polymorphic hemihydrate form F of sodium neridronate of about 400 mg per filmed tablet (expressed as free neridronic acid).

The amounts of excipients contained in each filmed tablet are listed in the following Table 10:

TABLE 10

| Composition F. | |
|---|---|
| Component | Unitary Amount |
| Crystalline polymorphic hemihydrate form F of sodium neridronate | 444.72 mg (corresponding to about 400 mg of free neridronic acid) |
| Polyvinylpyrrolidone | 12.00 mg |
| Microcrystalline cellulose | 118.00 mg |
| Croscarmellose | 12.00 mg |
| Talc | 40.00 mg |
| Magnesium Stearate | 6.00 mg |
| Methylhydroxypropylcellulose | 12.50 mg |
| Titanium dioxide | 6.25 mg |
| Polyethylene glycol 400 | 1.25 mg |

The bulk of composition F was prepared, in the desired amount and respecting the weight ratios listed in Table 10, following exactly the same method described in the previous Example 12, up to the compression step of the formulation.

Once said compression step was carried out, the obtained tablets were filmed using a filming lacquer prepared by suspending methylhydroxypropylcellulose, titanium dioxide and polyethylene glycol 400 in purified water.

Example 14. Pharmaceutical Composition of Crystalline Polymorphic Hemihydrate Form F of Sodium Neridronate for the Preparation of Pharmaceutical Forms for Parenteral Use in the Form of an Injectable Liquid Crystalline polymorphic hemihydrate form F of sodium neridronate may be effectively used also for the preparation of injectable pharmaceutical forms for parenteral use.

In order to produce a pharmaceutical composition for parenteral use, which can be administered in the form of an injectable liquid, the crystalline polymorphic hemihydrate form F of sodium neridronate was mixed with suitable excipients in an aqueous solvent.

The composition made, designated as composition G, contained a unitary dosage of crystalline polymorphic hemihydrate form F of sodium neridronate of about 100 mg per vial of injectable solution (expressed as free neridronic acid).

The amounts of excipients contained in each disposable vial are listed in the following Table 11:

TABLE 11

| Composition G. | |
| --- | --- |
| Component | Amount |
| Crystalline polymorphic hemihydrate form F of sodium neridronate | 111.18 mg (corresponding to about 100 mg of free neridronic acid) |
| Sodium chloride | 15.2 mg |
| Sodium citrate dihydrate | 102.92 mg |
| Citric acid monohydrate | 31.48 mg |
| Water for injectable preparations | q.s. to 8 mL |

The bulk of composition G was prepared, in the desired amounts and respecting the weight ratios listed in Table 11, according to the following method.

The desired amount of crystalline polymorphic hemihydrate form F of sodium neridronate was added to water for injectables, under magnetic stirring at maximum speed, until complete dissolution of the powder.

Sodium chloride, sodium citrate dihydrate and citric acid monohydrate were then added to the clear solution under magnetic stirring, until complete dissolution. After determining the pH value of the clear solution thus obtained, to be maintained in the range from 4.5 to 5.5, any deviations were adjusted by appropriate additions of either a 1 M sodium hydroxide or 1 M hydrochloric acid solution.

After the optional pH adjustment, the solution was added with water up to the desired volume, and the pH was checked and optionally adjusted again. Finally, the solution was assessed from a chemical and microbiological point of view, sterilized and bottled.

The crystalline polymorphic hemihydrate form F of sodium neridronate was therefore found to be a particularly stable crystalline form, suitable for use in the preparation of pharmaceutical compositions both for solid oral forms and liquid injectable forms, readily obtainable starting from sodium neridronate in any crystalline form available, by using a simple, low-cost, easily industrially scalable and reproducible synthetic method.

The invention claimed is:

1. A crystalline hemihydrate form F of sodium neridronate, characterized by an X-ray powder diffraction spectrum (XRPD) with characteristic peaks at 2θ angle values of 6.51°, 12.02°, 16.51°, 16.66°, 20.80°, 22.21°, 25.30°, 27.65°, 30.05°, 31.87°.

2. A crystalline hemihydrate form F of sodium neridronate having an X-ray powder diffraction spectrum (XRPD) as shown in FIG. 3.

3. A crystalline hemihydrate form F of sodium neridronate having a monoclinic crystal cell, belonging to the P21/c space group, and having the following cell parameters: a=14.3749 (3) Å, b=8.76600 (10) Å, c=21.2927 (4) Å, α=90°, β=109.339 (2)°, γ=90°, V=2531.71 (8) Å$^3$.

4. A process for the preparation of the crystalline hemihydrate form F of sodium neridronate according to claim 1 comprising the following steps:
 1) dissolving solid sodium neridronate in any crystalline form in water, at a temperature in the range from 70 to 90° C., to obtain an aqueous solution of sodium neridronate;
 2) adding a solvent selected from the group consisting in ethanol, 1-propanol, and 2-propanol to the aqueous solution obtained from step (1), so that the final water:solvent volume ratio is in the range from 1:0.5 to 1:1, thus obtaining a suspension;
 3) placing the suspension obtained from step (2) under mechanical stirring, at a temperature in the range from 60 to 95° C.;
 4) recovering the crystalline hemihydrate form F of sodium neridronate formed in the previous step (3).

5. The process according to claim 4, wherein the solvent of step (2) is ethanol.

6. The process according to claim 4, wherein step (3) is carried out at a temperature in the range from 70 to 90° C.

7. The process according to claim 4, wherein step (3) is maintained for a period of time in the range from 2 to 80 hours.

8. The process according to claim 4, wherein in step (2) the solvent is ethanol and the final water:ethanol volume ratio is in the range from 1:0.50 to 1:0.80.

9. A process for the preparation of sodium neridronate in any crystalline form, comprising the following steps:
 a) reacting 6-aminohexanoic acid with a mixture of phosphorous acid and methanesulfonic acid, and obtain a mixture;
 b) adding phosphorus trichloride to said mixture in step (a), under stirring and at a temperature in the range from 60 to 80° C., keeping the mixture obtained under stirring at a temperature in the range from 60 to 70° C. for at least 15 hours;
 c) diluting the mixture obtained in the previous step (b) with water, and heating said mixture diluted with water to a temperature in the range from 90 to 120° C. for at least 13 hours, obtaining a heated mixture;
 d) cooling the heated mixture obtained from step (c) to a temperature below 75° C., and slowly adding sodium hydroxide to a pH in the range from 3 to 5, obtaining a suspension;
 e) cooling the suspension obtained in step (d) to a temperature in the range from 10 to 30° C., then slowly adding ethanol to obtain the precipitation of the sodium salt of sodium neridronate in any crystalline form;
 f) recovering the sodium neridronate in any crystalline form formed in the previous step (e).

10. The process according to claim 9, wherein in step (a) the phosphorous acid and methanesulfonic acid mixture has a 1:1 stoichiometric ratio between the phosphorous acid equivalents and the 6-aminohexanoic acid equivalents.

11. The process according to claim 9, wherein in step (a) the 6-aminohexanoic acid is added into the reactor containing the phosphorous acid and methanesulfonic acid mixture at a temperature in the range from 20 to 30° C.

12. The process according to claim 9, wherein the sodium hydroxide in step (d) is added until the reaction mixture reaches a pH value in the range from about 4.0 to about 5.0.

13. A process for the preparation of the crystalline hemihydrate form F of sodium neridronate according to claim 1, comprising the following steps:
- (i) carrying out the process for the preparation of sodium neridronate in any crystalline form, said process comprising:
  - a) reacting 6-aminohexanoic acid with a mixture of phosphorous acid and methanesulfonic acid, and obtain a mixture;
  - b) adding phosphorus trichloride to said mixture in step (a), under stirring and at a temperature in the range from 60 to 80° C., keeping the mixture obtained under stirring at a temperature in the range from 60 to 70° C. for at least 15 hours;
  - c) diluting the mixture obtained in the previous step (b) with water, and heating said mixture diluted with water to a temperature in the range from 90 to 120° C. for at least 13 hours, obtaining a heated mixture;
  - d) cooling the heated mixture obtained from step (c) to a temperature below 75° C., and slowly adding sodium hydroxide to a pH in the range from 3 to 5, obtaining a suspension;
  - e) cooling the suspension obtained in step (d) to a temperature in the range from 10 to 30° C., then slowly adding ethanol to obtain the precipitation of the sodium salt of sodium neridronate in any crystalline form;
  - f) recovering the sodium neridronate in any crystalline form formed in the previous step (e); and
- (ii) carrying out the process for the preparation of the crystalline hemihydrate form F of sodium neridronate, said process comprising
  1) dissolving solid sodium neridronate in any crystalline form in water, at a temperature in the range from 70 to 90° C., to obtain an aqueous solution of sodium neridronate;
  2) adding a solvent selected from the group consisting in ethanol, 1-propanol, and 2-propanol to the aqueous solution obtained from step (1), so that the final water:solvent volume ratio is in the range from 1:0.5 to 1:1, thus obtaining a suspension;
  3) placing the suspension obtained from step (2) under mechanical stirring, at a temperature in the range from 60 to 95° C.;
  4) recovering the crystalline hemihydrate form F of sodium neridronate formed in the previous step (3).

14. A pharmaceutical composition comprising the crystalline hemihydrate form F of sodium neridronate according to claim 1, and pharmaceutically acceptable excipients.

15. A method of treating musculoskeletal and calcium metabolism disorders in patients in need thereof with a pharmaceutical composition comprising the crystalline hemihydrate form F of sodium neridronate according to claim 1, and pharmaceutically acceptable excipients, said method comprising administering a pharmaceutically effective amount of said composition to said patients and treating said musculoskeletal and calcium metabolism disorders.

16. The method according to claim 15, wherein said composition is administered orally in solid form, preferably tablet, capsule, cachet, pill, granule, or powder, comprising a unitary amount of crystalline hemihydrate form F of sodium neridronate, expressed as free neridronic acid, in the range from 50 to 500 mg.

17. The method according to claim 15 to be administered orally in liquid form.

18. The method according to claim 15 to be administered topically, rectally, vaginally, parenterally, nasally, or by aerosol.

19. The method according to claim 18 to be administered parenterally, preferably intramuscularly or intravenously, comprising a unitary amount of crystalline hemihydrate form F of sodium neridronate, expressed as anhydrous sodium neridronate, in the range from 50 to 500 mg.

20. The method according to claim 15, wherein said musculoskeletal and calcium metabolism disorders are selected from the group consisting in osteoporosis, hyperparathyroidism, hypercalcemia of malignancy, osteolytic bone metastases, myositis ossificans progressiva, universal calcinosis, arthritis, neuritis, bursitis, tendinitis, Paget's disease, osteogenesis imperfecta, Complex Regional Pain Syndrome (CRPS) and other inflammatory diseases.

* * * * *